US012593993B2

(12) United States Patent
Brooks et al.

(10) Patent No.:  US 12,593,993 B2
(45) Date of Patent:      Apr. 7, 2026

(54) DEVICES, METHODS AND SYSTEMS FOR MEASURING PULSE WAVE VELOCITY

(71) Applicant: QUALCOMM Incorporated, San Diego, CA (US)

(72) Inventors: Emily Kathryn Brooks, Amherst, NY (US); John Keith Schneider, Williamsville, NY (US); Hrishikesh Vijaykumar Panchawagh, Cupertino, CA (US); Nicholas Buchan, San Jose, CA (US); Evan Michael Breloff, Kenmore, NY (US); Ye Zhan, Buffalo, NY (US); Vivekananda Parampalli Adiga, Williamsville, NY (US); Shounak Uday Gore, Telangana (IN); Bernard Herrera Soukup, Sunnyvale, CA (US)

(73) Assignee: QUALCOMM Incorporated, San Diego, CA (US)

( * ) Notice: Subject to any disclaimer, the term of this patent is extended or adjusted under 35 U.S.C. 154(b) by 258 days.

(21) Appl. No.: 18/339,162

(22) Filed: Jun. 21, 2023

(65) Prior Publication Data

US 2024/0423487 A1      Dec. 26, 2024

(51) Int. Cl.
*A61B 5/00*          (2006.01)
*A61B 5/02*          (2006.01)
*A61B 5/021*         (2006.01)

(52) U.S. Cl.
CPC ........ *A61B 5/02108* (2013.01); *A61B 5/0095* (2013.01); *A61B 5/02007* (2013.01); *A61B 5/6801* (2013.01); *A61B 2562/046* (2013.01)

(58) Field of Classification Search
CPC .............. A61B 5/02108; A61B 5/0095; A61B 5/02007; A61B 5/6801; A61B 2562/046; A61B 5/681; A61B 5/02125
See application file for complete search history.

(56) References Cited

U.S. PATENT DOCUMENTS 11,766,196 B1 *  9/2023  Davis ................. A61B 5/14535
                                                                  600/316
12,023,180 B1     7/2024  Miller et al.
                          (Continued)

FOREIGN PATENT DOCUMENTS

WO       2022125171       6/2022

OTHER PUBLICATIONS

Ross Williams, Andrew Needles, Emmanuel Cherin, Yu-Qing Zhou, R. Mark Henkelman, S. Lee Adamson, F. Stuart Foster, Noninvasive Ultrasonic Measurement of Regional and Local Pulse-Wave Velocity in Mice, Ultrasound in Medicine & Biology, vol. 33, Issue 9, 2007, pp. 1368-1375, ISSN 0301-5629, (Year: 2007).*
(Continued)

*Primary Examiner* — Joel Lamprecht
(74) *Attorney, Agent, or Firm* — QUALCOMM Incorporated

(57)          ABSTRACT

Some disclosed devices include a light source system, an ultrasonic receiver system and a control system. The control system may be configured to receive first sensor signals, including ultrasonic receiver signals, from the ultrasonic receiver system and to estimate one or more blood vessel features based on the first sensor signals. The control system may be configured to receive second sensor signals from a second sensor and to estimate a PWV based on the first sensor signals and the second sensor signals. The control system may be configured to estimate blood pressure based, at least in part, on the one or more blood vessel features and the PWV.

28 Claims, 12 Drawing Sheets

(56)                     References Cited

U.S. PATENT DOCUMENTS

2014/0081098 A1*    3/2014    Cohrs .................... A61B 5/029
                                                          600/324
2022/0175258 A1     6/2022    Kitchens et al.

OTHER PUBLICATIONS

D. B. McCombie, A. T. Reisner and H. H. Asada, "Adaptive blood pressure estimation from wearable PPG sensors using peripheral artery pulse wave velocity measurements and multi-channel blind identification of local arterial dynamics," 2006 International Conference of the IEEE Engineering in Medicine (Year: 2006).*
International Search Report and Written Opinion—PCT/US2024/027110—ISA/EPO—Jul. 19, 2024.

* cited by examiner

100

Platen — 101

Ultrasonic Receiver System — 102

Light Source System — 104

Control System — 106

Interface System — 108

Noise Reduction System — 110

Sensor 1
205a

Sensor 2
205b

Sensor 1
205a

Sensor 2
205b

700

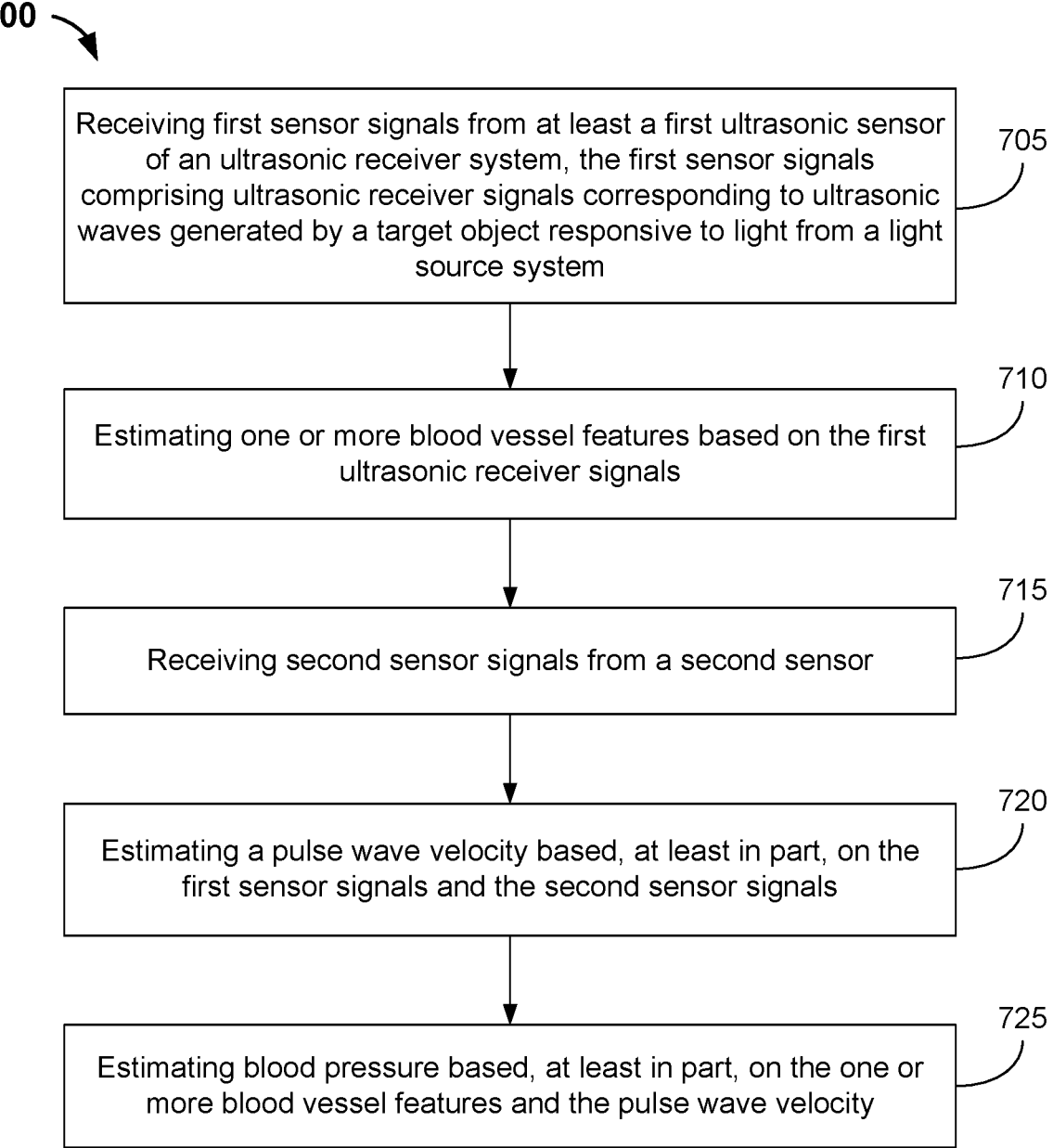

Receiving first sensor signals from at least a first ultrasonic sensor of an ultrasonic receiver system, the first sensor signals comprising ultrasonic receiver signals corresponding to ultrasonic waves generated by a target object responsive to light from a light source system    705

Estimating one or more blood vessel features based on the first ultrasonic receiver signals    710

Receiving second sensor signals from a second sensor    715

Estimating a pulse wave velocity based, at least in part, on the first sensor signals and the second sensor signals    720

Estimating blood pressure based, at least in part, on the one or more blood vessel features and the pulse wave velocity    725

*Figure 7*

DEVICES, METHODS AND SYSTEMS FOR MEASURING PULSE WAVE VELOCITY

TECHNICAL FIELD

This disclosure relates generally to measuring pulse wave velocity and more specifically to measuring pulse wave velocity with devices configured to be worn by, or attached to, a person.

DESCRIPTION OF RELATED TECHNOLOGY

A variety of different sensing technologies and algorithms are being implemented in devices for various biometric and biomedical applications, including health and wellness monitoring. This push is partly a result of the limitations in the usability of traditional measuring devices for continuous, noninvasive and ambulatory monitoring. Some such devices may be, or include, photoacoustic devices. Although some previously-deployed devices and systems can provide acceptable results, improved devices and systems would be desirable.

SUMMARY

The systems, methods and devices of this disclosure each have several aspects, no single one of which is solely responsible for the desirable attributes disclosed herein.

One innovative aspect of the subject matter described in this disclosure can be implemented in an apparatus. The apparatus may include a light source system and a receiver system. The light source system may be configured for providing light to a target object on an outer surface of the apparatus The receiver system may be, or may include, an ultrasonic receiver system. The receiver system may be configured to receive ultrasonic waves generated by the target object responsive to the light from the light source system. In some implementations, a mobile device (such as a wearable device, a cellular telephone, etc.) may be, or may include, at least part of the apparatus.

In some implementations, the apparatus may include a control system. The control system may include one or more general purpose single- or multi-chip processors, digital signal processors (DSPs), application specific integrated circuits (ASICs), field programmable gate arrays (FPGAs) or other programmable logic devices, discrete gates or transistor logic, discrete hardware components, or combinations thereof. According to some examples, the control system may be configured to receive first sensor signals from at least a first ultrasonic sensor of the ultrasonic receiver system. The first sensor signals may be, or may include, ultrasonic receiver signals. In some examples, the control system may be configured to estimate one or more blood vessel features based on the first sensor signals. According to some examples, the control system may be configured to receive second sensor signals from a second sensor, or from a second sensor system. In some examples, the control system may be configured to estimate a pulse wave velocity based, at least in part, on the first sensor signals and the second sensor signals. According to some examples, the control system may be configured to estimate blood pressure based, at least in part, on the one or more blood vessel features and the pulse wave velocity.

According to some examples, the apparatus may be configured to be worn by, or attached to, a person. In some examples, the apparatus may be, or may include, a watch, an ear bud, headphones, an ear clip, a chest strap, an arm strap, a head band, or eye wear. In some examples, the apparatus may be configured to be worn on the person's wrist. According to some examples, the second device may be configured to be worn by, or attached to, the person's finger or the person's arm.

In some examples, the second sensor signals may include signals from a photoplethysmography sensor, signals from a photoacoustic plethysmography sensor, microphone signals, signals from an accelerometer, capacitive sensor signals, signals from a radio frequency sensor, signals from a magnetic sensor, electrocardiogram signals, signals from an ultrasonic sensor, signals from a pressure sensor, signals from a camera, or combinations thereof.

According to some examples, the apparatus also may include an interface system In some examples, the second sensor signals may be received, via the interface system, from a second device. In some examples, the control system may be further configured to estimate a distance between the first ultrasonic sensor and the second sensor. According to some examples, the second sensor may be a component of the ultrasonic receiver system. In some examples, the apparatus may be a component of a weighing scale, a component of an automobile, a component of an exercise machine or a component of a game controller.

According to some examples, the one or more blood vessel features may include blood vessel diameter, blood vessel distension, volumetric flow, or combinations thereof. In some examples, the ultrasonic receiver system may include an array of ultrasonic receiver elements.

In some examples, the pulse wave velocity may be a regional pulse wave velocity and the control system may be further configured to estimate a local pulse wave velocity. According to some examples, the second sensor signals may include signals from a sensor array. In some examples, the sensor array may be a two-dimensional sensor array.

Other innovative aspects of the subject matter described in this disclosure can be implemented in one or more methods. Some such methods may involve receiving first sensor signals from at least a first ultrasonic sensor of an ultrasonic receiver system. In some examples, the first sensor signals may be, or may include, ultrasonic receiver signals corresponding to ultrasonic waves generated by a target object responsive to light from a light source system. Some methods may involve estimating one or more blood vessel features based on the first ultrasonic receiver signals. Some methods may involve receiving second sensor signals from a second sensor, estimating a pulse wave velocity based, at least in part, on the first ultrasonic receiver signals and the second sensor signals and estimating blood pressure based, at least in part, on the one or more blood vessel features and the pulse wave velocity. Some methods may involve estimating a distance between the first ultrasonic sensor and the second sensor.

According to some examples, the second sensor signals may be received from a second device. In some examples, the first sensor signals may correspond to ultrasonic waves generated within a person's wrist. According to some examples, the second sensor signals may be obtained from the person's finger or the person's arm. According to some examples, the second sensor signals may include signals from a photoplethysmography sensor, signals from a photoacoustic plethysmography sensor, microphone signals, signals from an accelerometer, capacitive sensor signals, signals from a radio frequency sensor, signals from a magnetic sensor, electrocardiogram signals, signals from an ultrasonic sensor, signals from a pressure sensor, signals from a camera, or combinations thereof.

In some examples, the pulse wave velocity may be a regional pulse wave velocity. According to some examples, the method may involve estimating a local pulse wave velocity.

According to some examples, the second sensor signals may include signals from a sensor array. In some examples, the sensor array may be a two-dimensional sensor array. According to some examples, the one or more blood vessel features may include blood vessel diameter, blood vessel distension, volumetric flow, or combinations thereof. According to some examples, receiving the first sensor signals may involve receiving signals from an array of ultrasonic sensors of the ultrasonic receiver system.

Some or all of the methods described herein may be performed by one or more devices according to instructions (e.g., software) stored on non-transitory media. Such non-transitory media may include memory devices such as those described herein, including but not limited to random access memory (RAM) devices, read-only memory (ROM) devices, etc. Accordingly, some innovative aspects of the subject matter described in this disclosure can be implemented in one or more non-transitory media having software stored thereon. The software may include instructions for controlling one or more devices to perform one or more disclosed methods.

Some such methods may involve receiving first sensor signals from at least a first ultrasonic sensor of an ultrasonic receiver system. In some examples, the first sensor signals may be, or may include, ultrasonic receiver signals corresponding to ultrasonic waves generated by a target object responsive to light from a light source system. Some methods may involve estimating one or more blood vessel features based on the first ultrasonic receiver signals. Some methods may involve receiving second sensor signals from a second sensor, estimating a pulse wave velocity based, at least in part, on the first ultrasonic receiver signals and the second sensor signals and estimating blood pressure based, at least in part, on the one or more blood vessel features and the pulse wave velocity. Some methods may involve estimating a distance between the first ultrasonic sensor and the second sensor.

According to some examples, the second sensor signals may be received from a second device. In some examples, the first sensor signals may correspond to ultrasonic waves generated within a person's wrist. According to some examples, the second sensor signals may be obtained from the person's finger or the person's arm. According to some examples, the second sensor signals may include signals from a photoplethysmography sensor, signals from a photoacoustic plethysmography sensor, microphone signals, signals from an accelerometer, capacitive sensor signals, signals from a radio frequency sensor, signals from a magnetic sensor, electrocardiogram signals, signals from an ultrasonic sensor, signals from a pressure sensor, signals from a camera, or combinations thereof.

In some examples, the pulse wave velocity may be a regional pulse wave velocity. According to some examples, the method may involve estimating a local pulse wave velocity.

According to some examples, the second sensor signals may include signals from a sensor array. In some examples, the sensor array may be a two-dimensional sensor array. According to some examples, the one or more blood vessel features may include blood vessel diameter, blood vessel distension, volumetric flow, or combinations thereof. According to some examples, receiving the first sensor signals may involve receiving signals from an array of ultrasonic sensors of the ultrasonic receiver system.

Details of one or more implementations of the subject matter described in this disclosure are set forth in the accompanying drawings and the description below. Other features, aspects, and advantages will become apparent from the description, the drawings and the claims. Note that the relative dimensions of the following figures may not be drawn to scale.

BRIEF DESCRIPTION OF THE DRAWINGS

FIG. 7 is a flow diagram that shows examples of some disclosed operations.

Like reference numbers and designations in the various drawings indicate like elements.

DETAILED DESCRIPTION

Figure 1:
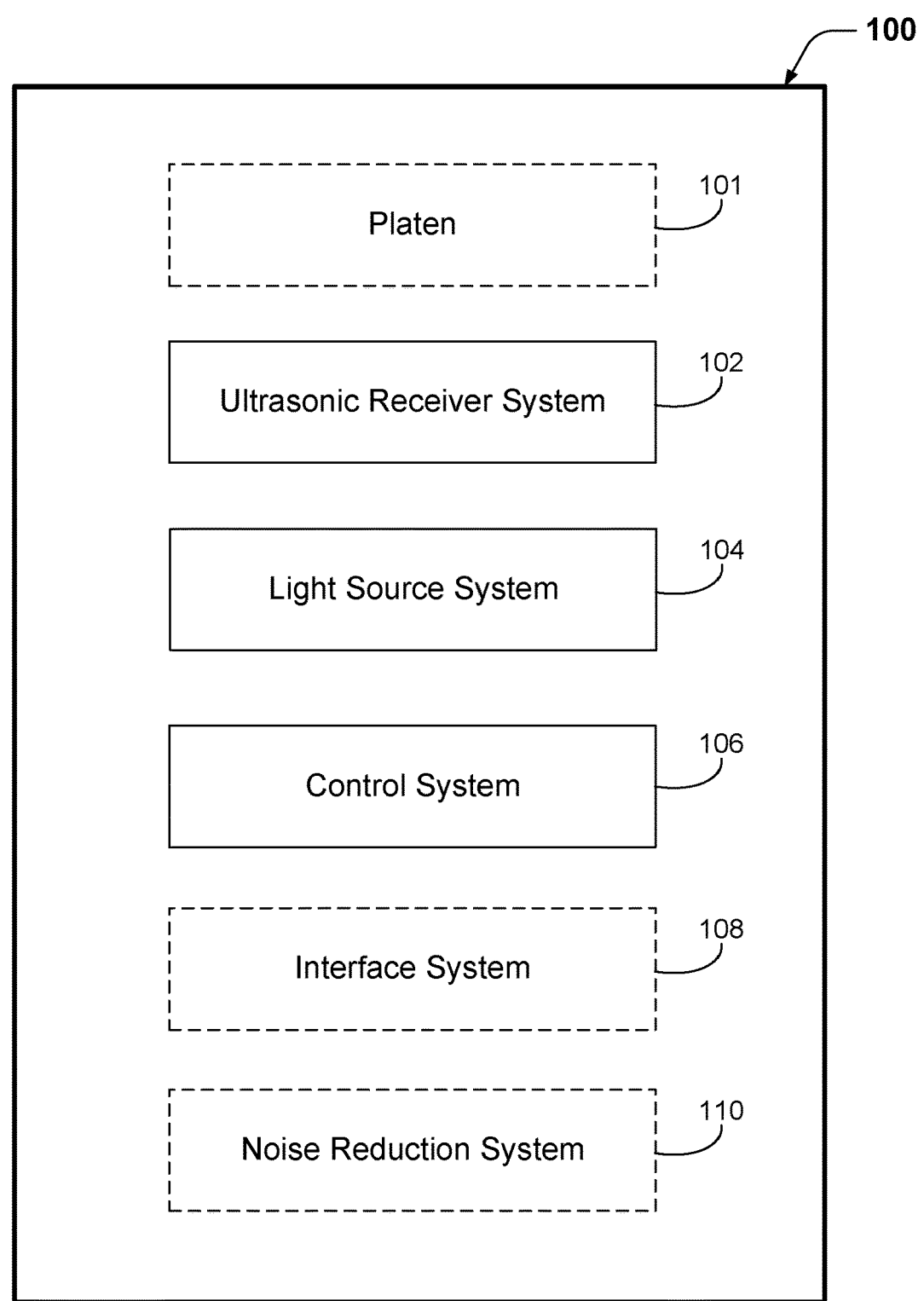
FIG. 1 is a block diagram that shows example components of an apparatus according to some disclosed implementations.

The following description is directed to certain implementations for the purposes of describing various aspects of this disclosure. However, a person having ordinary skill in the art will readily recognize that the teachings herein can be applied in a multitude of different ways. Some of the concepts and examples provided in this disclosure are especially applicable to blood pressure monitoring applications. However, some implementations also may be applicable to other types of biological sensing applications, as well as to other fluid flow systems. The described implementations may be implemented in any device, apparatus, or system that includes an apparatus as disclosed herein. In addition, it is contemplated that the described implementations may be included in or associated with a variety of electronic devices such as, but not limited to: mobile telephones, multimedia Internet enabled cellular telephones, mobile television receivers, wireless devices, smartphones, smart cards, wearable devices such as bracelets, armbands, wristbands, rings, headbands, patches, etc., Bluetooth® devices, personal data assistants (PDAs), wireless electronic mail receivers, hand-held or portable computers, netbooks, notebooks, smart-books, tablets, printers, copiers, scanners, facsimile devices, global positioning system (GPS) receivers/navigators, cameras, digital media players, game consoles, wrist watches, clocks, calculators, television monitors, flat panel displays, electronic reading devices (e.g., e-readers), mobile health devices, computer monitors, auto displays (including odometer and speedometer displays, etc.), cockpit controls and/or displays, camera view displays (such as the display of a rear view camera in a vehicle), architectural structures, micro-waves, refrigerators, stereo systems, cassette recorders or players, DVD players, CD players, VCRs, radios, portable memory chips, washers, dryers, washer/dryers, parking meters, automobile doors, autonomous or semi-autonomous vehicles, drones, Internet of Things (IoT) devices, etc. Thus, the teachings are not intended to be limited to the specific implementations depicted and described with reference to the drawings; rather, the teachings have wide applicability as will be readily apparent to persons having ordinary skill in the art.

Non-invasive health monitoring devices have various potential advantages over more invasive health monitoring devices such as cuff-based or catheter-based blood pressure measurement devices. However, it has proven to be difficult to design satisfactory wearable devices that are capable of estimating cardiac-related features, such as blood pressure. Some methods for estimating blood pressure require accurate pulse wave velocity (PWV) measurements. One challenge of obtaining accurate PWV measurements with wearable devices is that two-point or multi-point measurements along an artery are needed. However, most wearable health monitoring devices have compact designs, which makes it difficult to place the sensors of such devices along a blood vessel to obtain a precise PWV measurement.

Some disclosed devices include a light source system, an ultrasonic receiver system and a control system. The control system may be configured to receive first sensor signals from at least a first ultrasonic sensor of the ultrasonic receiver system. The first sensor signals may be, or may include, ultrasonic receiver signals. The control system may be configured to estimate one or more blood vessel features based on the first sensor signals. The one or more blood vessel features include blood vessel diameter, blood vessel distension, volumetric flow, or combinations thereof.

The control system may be configured to receive second sensor signals from a second sensor, or from a second sensor system. The control system may be configured to estimate a PWV based, at least in part, on the first sensor signals and the second sensor signals. If the second sensor system resides more than 50 millimeters from at least the first ultrasonic sensor of the ultrasonic receiver system, the PWV may be considered to be a regional PWV. If the second sensor system resides less than 50 millimeters from at least the first ultrasonic sensor of the ultrasonic receiver system, the PWV may be considered to be a local PWV. The control system may be configured to estimate blood pressure based, at least in part, on the one or more blood vessel features and the PWV.

Particular implementations of the subject matter described in this disclosure can be implemented to realize one or more of the following potential advantages. Various disclosed configurations are capable of obtaining accurate PWV measurements and accurate measurements of one or more blood vessel features such as blood vessel diameter, blood vessel distension, etc. Accordingly, measurements from such devices may be used to obtain accurate estimates of blood pressure.

FIG. 1 is a block diagram that shows example components of an apparatus according to some disclosed implementations. In this example, the apparatus 100 includes an ultrasonic receiver system 102, a control system 106 and a light source system 104. Some implementations of the apparatus 100 may include a platen 101, an interface system 108, a noise reduction system 110, or combinations thereof. As with other disclosed implementations, in some alternative implementations the apparatus 100 may include more components, fewer components, different components, or combinations thereof.

In some implementations, the platen 101—if present—may be configured to increase an intensity of ultrasonic energy received by at least a portion of the ultrasonic receiver system. In some such implementations, the platen 101 may include an acoustic waveguide. According to some implementations, the platen 101 may include an acoustic lens system. The acoustic lens system may, for example, reside on, or proximate, an outer surface of the platen 101. The acoustic lens system may, for example, include a spherical lens or a cylindrical lens.

According to some examples, the platen 101 (or another portion of the apparatus) may include one or more anti-reflective layers. In some examples, one or more anti-reflective layers may reside on, or proximate, one or more outer surfaces of the platen 101.

In some examples, at least a portion of the outer surface of the platen 101 may have an acoustic impedance that is configured to approximate an acoustic impedance of human skin. The portion of the outer surface of the platen 101 may, for example, be a portion that is configured to receive a target object, such as a human digit. (As used herein, the terms "finger" and "digit" may be used interchangeably, such that a thumb is one example of a finger.) A typical range of acoustic impedances for human skin is 1.53-1.680 MRayls. In some examples, at least an outer surface of the platen 101 may have an acoustic impedance that is in the range of 1.4-1.8 MRayls, or in the range of 1.5-1.7 MRayls.

Alternatively, or additionally, in some examples at least an outer surface of the platen 101 may be configured to conform to a surface of human skin. In some such examples, at least an outer surface of the platen 101 may have material properties like those of putty or chewing gum.

In some examples, at least a portion of the platen 101 may have an acoustic impedance that is configured to approximate an acoustic impedance of one or more receiver elements of the ultrasonic receiver system 102. According to some examples, a layer residing between the platen 101 and one or more receiver elements may have an acoustic impedance that is configured to approximate an acoustic impedance of the one or more receiver elements. Alternatively, or additionally, in some examples a layer residing between the platen 101 and one or more receiver elements may have an acoustic impedance that is in an acoustic impedance range between an acoustic impedance of the platen and an acoustic impedance of the one or more receiver elements.

In this example, the ultrasonic receiver system 102 includes one or more ultrasonic receiver elements. Various examples and configurations of ultrasonic receiver systems 102 are disclosed herein. In some examples, the ultrasonic receiver system 102 may include an array of ultrasonic receiver elements. According to some such examples, the ultrasonic receiver system 102 may include a two-dimensional array of ultrasonic receiver elements. In some examples, the ultrasonic receiver system 102 may include an array of electrodes arranged on a piezoelectric receiver layer, such as a layer of PVDF polymer, a layer of PVDF-TrFE copolymer, or a layer of piezoelectric composite material. In some implementations, other piezoelectric materials may be used in the piezoelectric layer, such as aluminum nitride (AlN) or lead zirconate titanate (PZT). The ultrasonic receiver system 102 may, in some examples, include an array of ultrasonic transducer elements, such as an array of piezoelectric micromachined ultrasonic transducers (PMUTs), an array of capacitive micromachined ultrasonic transducers (CMUTs), etc. In some such examples, a piezoelectric receiver layer, PMUT elements in a single-layer array of PMUTs, or CMUT elements in a single-layer array of CMUTs, may be used as ultrasonic transmitters as well as ultrasonic receivers. According to some examples, the ultrasonic receiver system 102 may be, or may include, an ultrasonic receiver array. In some examples, the apparatus 100 may include one or more separate ultrasonic transmitter elements. In some such examples, the ultrasonic transmitter(s) may include an ultrasonic plane-wave generator.

According to some implementations, the light source system 104 may include one or more light-emitting diodes (LEDs). In some implementations, the light source system 104 may include one or more laser diodes. According to some implementations, the light source system 104 may include one or more vertical-cavity surface-emitting lasers (VCSELs). In some implementations, the light source system 104 may include one or more edge-emitting lasers. In some implementations, the light source system may include one or more neodymium-doped yttrium aluminum garnet (Nd:YAG) lasers. The light source system 104 may, in some examples, include an array of light-emitting elements, such as an array of LEDs, an array of laser diodes, an array of VCSELs, an array of edge-emitting lasers, or combinations thereof.

The light source system 104 may, in some examples, be configured to transmit light in one or more wavelength ranges. In some examples, the light source system 104 may configured for transmitting light in a wavelength range of 500 to 600 nanometers. According to some examples, the light source system 104 may configured for transmitting light in a wavelength range of 800 to 950 nanometers.

The light source system 104 may include various types of drive circuitry, depending on the particular implementation. In some disclosed implementations, the light source system 104 may include at least one multi-junction laser diode, which may produce less noise than single-junction laser diodes. In some examples, the light source system 104 may include a drive circuit (also referred to herein as drive circuitry) configured to cause the light source system to emit pulses of light at pulse widths in a range from 3 nanoseconds to 1000 nanoseconds. According to some examples, the light source system 104 may include a drive circuit configured to cause the light source system to emit pulses of light at pulse repetition frequencies in a range from 1 kilohertz to 100 kilohertz.

In some implementations, the light source system 104 may be configured for emitting various wavelengths of light, which may be selectable to trigger acoustic wave emissions primarily from a particular type of material. For example, because the hemoglobin in blood absorbs near-infrared light very strongly, in some implementations the light source system 104 may be configured for emitting one or more wavelengths of light in the near-infrared range, in order to trigger acoustic wave emissions from hemoglobin. However, in some examples the control system 106 may control the wavelength(s) of light emitted by the light source system 104 to preferentially induce acoustic waves in blood vessels, other soft tissue, and/or bones. For example, an infrared (IR) light-emitting diode LED may be selected and a short pulse of IR light emitted to illuminate a portion of a target object and generate acoustic wave emissions that are then detected by the ultrasonic receiver system 102. In another example, an IR LED and a red LED or other color such as green, blue, white or ultraviolet (UV) may be selected and a short pulse of light emitted from each light source in turn with ultrasonic images obtained after light has been emitted from each light source. In other implementations, one or more light sources of different wavelengths may be fired in turn or simultaneously to generate acoustic emissions that may be detected by the ultrasonic receiver. Image data from the ultrasonic receiver that is obtained with light sources of different wavelengths and at different depths (e.g., varying RGDs) into the target object may be combined to determine the location and type of material in the target object. Image contrast may occur as materials in the body generally absorb light at different wavelengths differently. As materials in the body absorb light at a specific wavelength, they may heat differentially and generate acoustic wave emissions with sufficiently short pulses of light having sufficient intensities. Depth contrast may be obtained with light of different wavelengths and/or intensities at each selected wavelength. That is, successive images may be obtained at a fixed RGD (which may correspond with a fixed depth into the target object) with varying light intensities and wavelengths to detect materials and their locations within a target object. For example, hemoglobin, blood glucose or blood oxygen within a blood vessel inside a target object such as a finger may be detected photoacoustically.

According to some implementations, the light source system 104 may be configured for emitting a light pulse with a pulse width less than about 100 nanoseconds. In some implementations, the light pulse may have a pulse width between about 10 nanoseconds and about 500 nanoseconds or more. According to some examples, the light source system may be configured for emitting a plurality of light pulses at a pulse repetition frequency between 10 Hz and 100 kHz. Alternatively, or additionally, in some implementations the light source system 104 may be configured for emitting a plurality of light pulses at a pulse repetition frequency between about 1 MHz and about 100 MHz. Alternatively, or additionally, in some implementations the light source system 104 may be configured for emitting a plurality of light pulses at a pulse repetition frequency between about 10 Hz and about 1 MHz. In some examples, the pulse repetition frequency of the light pulses may correspond to an acoustic resonant frequency of the ultrasonic receiver and the substrate. For example, a set of four or more light pulses may be emitted from the light source system 104 at a frequency that corresponds with the resonant frequency of a resonant acoustic cavity in the sensor stack, allowing a build-up of the received ultrasonic waves and a higher resultant signal strength. In some implementations, filtered light or light sources with specific wavelengths for detecting selected materials may be included with the light source system 104. In some implementations, the light source system may contain light sources such as red, green and blue LEDs of a display that may be augmented with light sources of other wavelengths (such as IR and/or UV) and with light sources of higher optical power. For example, high-power laser diodes or electronic flash units (e.g., an LED or xenon flash unit) with or without filters may be used for short-term illumination of the target object.

The control system 106 may include one or more general purpose single- or multi-chip processors, digital signal processors (DSPs), application specific integrated circuits (ASICs), field programmable gate arrays (FPGAs) or other programmable logic devices, discrete gates or transistor logic, discrete hardware components, or combinations thereof. The control system 106 also may include (and/or be configured for communication with) one or more memory devices, such as one or more random access memory (RAM) devices, read-only memory (ROM) devices, etc. Accordingly, the apparatus 100 may have a memory system that includes one or more memory devices, though the memory system is not shown in FIG. 1. The control system 106 may be configured for receiving and processing data from the ultrasonic receiver system 102, e.g., as described below. If the apparatus 100 includes an ultrasonic transmitter, the control system 106 may be configured for controlling the ultrasonic transmitter. In some implementations, functionality of the control system 106 may be partitioned between one or more controllers or processors, such as a dedicated sensor controller and an applications processor of a mobile device.

In some examples, the control system 106 may be configured to control the light source system 104 to emit light towards a target object on an outer surface of the apparatus 100. In some such examples, the control system 106 may be configured to receive signals from the ultrasonic receiver system 102 corresponding to ultrasonic waves generated by the target object responsive to the light from the light source system 104.

In some examples, the control system 106 may be configured to receive first sensor signals from at least a first ultrasonic sensor of the ultrasonic receiver system. The first sensor signals may be, or may include, ultrasonic receiver signals. In some such examples, the first sensor signals may be, or may include, ultrasonic receiver signals from an ultrasonic receiver array. The ultrasonic receiver array may include a linear array, a two-dimensional array, etc. Receiving the first sensor signals from an ultrasonic receiver array may be potentially advantageous, because such signals may allow for more reliable location of a blood vessel, such as an artery.

According to some examples, the control system 106 may be configured to estimate one or more blood vessel features based on the first sensor signals. The blood vessel feature(s) may include blood vessel diameter, blood vessel distension, volumetric flow, or combinations thereof.

In some examples, the control system 106 may be configured to receive second sensor signals from a second sensor, or from a second sensor system. The second sensor signals may be, or may include, signals from a photoplethysmography sensor, signals from a photoacoustic plethysmography sensor, microphone signals, signals from an accelerometer, capacitive sensor signals, signals from a radio frequency sensor, signals from a magnetic sensor, electrocardiogram signals, signals from an ultrasonic sensor, signals from a pressure sensor, signals from a camera, or combinations thereof. According to some examples the second sensor, or the second sensor system, may be part of the same apparatus that includes the ultrasonic receiver system 102. However, in other examples the second sensor, or the second sensor system, may be part of another apparatus. In some such examples, the second sensor signals may be, or may include, signals from a sensor array, signals from a receiver array, etc. The array may, in some examples, be a two-dimensional array.

According to some examples, the control system 106 may be configured to estimate a pulse wave velocity based, at least in part, on the first sensor signals and the second sensor signals. In some examples, the control system 106 may be configured to estimate one or more cardiac features based, at least in part, on the one or more blood vessel features and the pulse wave velocity. According to some examples, the cardiac features may be, or may include, blood pressure.

Some implementations of the apparatus 100 may include the interface system 108. In some examples, the interface system 108 may include a wireless interface system. In some implementations, the interface system 108 may include a user interface system, one or more network interfaces, one or more interfaces between the control system 106 and a memory system and/or one or more interfaces between the control system 106 and one or more external device interfaces (e.g., ports or applications processors), or combinations thereof. According to some examples in which the interface system 108 is present and includes a user interface system, the user interface system may include a microphone system, a loudspeaker system, a haptic feedback system, a voice command system, one or more displays, or combinations thereof. According to some examples, the interface system 108 may include a touch sensor system, a gesture sensor system, or a combination thereof. The touch sensor system (if present) may be, or may include, a resistive touch sensor system, a surface capacitive touch sensor system, a projected capacitive touch sensor system, a surface acoustic wave touch sensor system, an infrared touch sensor system, any other suitable type of touch sensor system, or combinations thereof.

In some examples, the interface system 108 may include, a force sensor system. The force sensor system (if present) may be, or may include, a piezo-resistive sensor, a capacitive sensor, a thin film sensor (for example, a polymer-based thin film sensor), another type of suitable force sensor, or combinations thereof. If the force sensor system includes a piezo-resistive sensor, the piezo-resistive sensor may include silicon, metal, polysilicon, glass, or combinations thereof. An ultrasonic fingerprint sensor and a force sensor system may, in some implementations, be mechanically coupled. In some such examples, the force sensor system may be integrated into circuitry of the ultrasonic fingerprint sensor. In some examples, the interface system 108 may include an optical sensor system, one or more cameras, or a combination thereof.

According to some examples, the apparatus 100 may include a noise reduction system 110. For example, the noise reduction system 110 may include one or more mirrors that are configured to reflect light from the light source system 104 away from the ultrasonic receiver system 102. In some implementations, the noise reduction system 110 may include one or more sound-absorbing layers, acoustic isolation material, light-absorbing material, light-reflecting material, or combinations thereof. In some examples, the noise reduction system 110 may include acoustic isolation material, which may reside between the light source system 104 and at least a portion of the ultrasonic receiver system 102, on at least a portion of the ultrasonic receiver system 102, or combinations thereof. In some examples, the noise reduction system 110 may include one or more electromagnetically shielded transmission wires. In some such examples, the one or more electromagnetically shielded transmission wires may be configured to reduce electromagnetic interference from circuitry of the light source system 104, receiver system circuitry, or combinations thereof, that is received by the ultrasonic receiver system 102. In some examples, the one or more electromagnetically shielded transmission wires, sound-absorbing layers, acoustic isolation material, light-absorbing material, light-reflecting material, or combinations thereof may be components of the ultrasonic receiver system 102, the light source system 104, or both. Despite the fact that the ultrasonic receiver system 102, the light source system 104 and the noise reduction system 110 are shown in FIG. 1 as being separate elements, such components may nonetheless be regarded as elements of the noise reduction system 110.

The apparatus 100 may be used in a variety of different contexts, many examples of which are disclosed herein. In some implementations, a wearable device may include the apparatus 100. The wearable device may be, or may include, a bracelet, one or more devices configured to be attached to an arm, such as an armband or an arm strap, one or more devices configured to be attached to a wrist, such as a wristband or a watch, one or more devices configured to be attached to a finger, such as a ring or a finger strap, a headband, one or more ear buds, headphones, one or more car clips, a chest strap, eye wear—such as glasses or goggles—or a patch. Accordingly, in some examples the apparatus 100 may be configured to be worn by, or attached to, a person.

However, in some examples, at least a portion of the apparatus 100 may not be configured to be worn by, or attached to, a person. For example, in some implementations a mobile device may include the apparatus 100. In some such examples, the mobile device may be, or may include, a smart phone. In some examples, the apparatus 100 may be, or may include, a component of a weighing scale, such as a component residing in or on a portion of the weighing scale that is configured to receive a person's foot or feet. According to some examples, the apparatus 100 may be, or may include, a component of an automobile, such as a component residing in or on a portion of a steering wheel, a door handle, an arm rest, etc. In some examples, the apparatus 100 may be, or may include, a component of an exercise machine, such as a component configured to receive a person's foot (such as a pedal), a component configured to receive a person's hand (such as a handle, a hand grip, a lever or a bar), etc. According to some examples, the apparatus 100 may be, or may include, a component of a game controller.

Figure 2A:
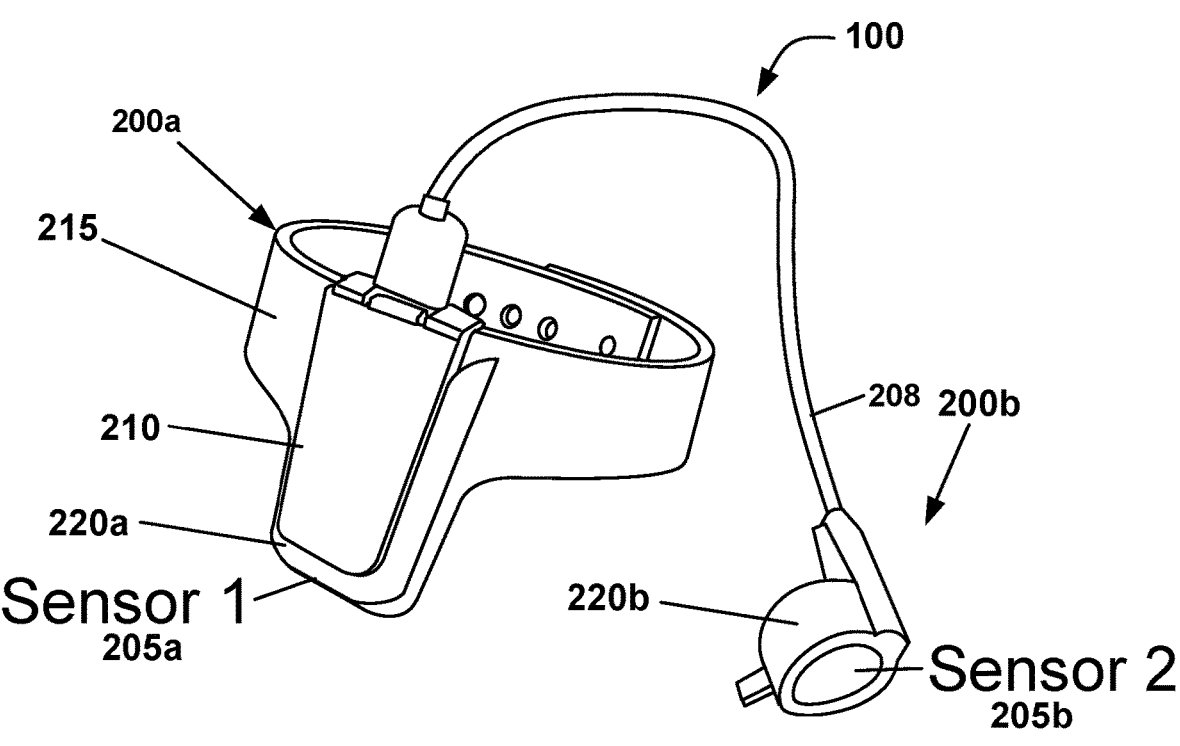
FIG. 2A shows components of an apparatus according to one example.

FIG. 2A shows components of an apparatus according to one example. In this example, the apparatus 100 includes apparatus portions 200a and 200b. In this example, the apparatus portion 200a is configured to be worn on a person's wrist. Accordingly, in this example the apparatus portion 200a includes a sensor 205a, an adjustable wrist band 215, a housing portion 220a and a display 210 that resides in or on a portion of the housing portion 220a. In this example, the apparatus portion 200b is configured to be worn on a person's finger and includes a sensor 205b. Here, the apparatus portion 200b is electrically connected to the apparatus portion 200a via the electrical interface 208. As with other disclosed examples, the types, numbers, sizes and arrangements of elements shown in FIG. 2A are merely examples.

The sensor 205a, which is also labeled as "Sensor 1" in FIG. 2A, is an example of what may be referred to herein as a first sensor, or a first sensor system. In this example, the sensor 205a resides within the housing portion 220a on a side of the housing portion 220a that faces a person's wrist when the adjustable wrist band 215 is fastened to the person's wrist. In other words, the display 210 resides in or on a first side of the housing portion 220a—which may be referred to as an outer side—and the sensor 205a resides in or on a second side of the housing portion 220a that faces a person's wrist when the adjustable wrist band 215 is fastened to the person's wrist. The second side may be referred to herein as an inner side.

In some examples, the sensor 205a may be, or may include, a PAPG sensor. However, in some examples the sensor 205a may be, or may include, another type of sensor, such as an ultrasonic sensor capable of transmitting and receiving ultrasonic waves. In some examples in which the sensor 205a is, or includes, a PAPG sensor, the sensor 205a may include instances of the ultrasonic receiver system 102, the light source system 104 and the control system 106 that are described with reference to FIG. 1. In some examples, the ultrasonic receiver system 102 may include a sensor array, which in some examples may be a two-dimensional sensor array. According to some examples, the control system 106 may be configured to control the light source system 104 to emit light towards the wrist of a person wearing the apparatus portion 200a.

In some examples, the control system 106 may be configured to receive first sensor signals from the ultrasonic receiver system 102. The first sensor signals may be ultrasonic receiver signals corresponding to ultrasonic waves generated by a blood vessel within the person's wrist, blood within the blood vessel, or a combination thereof, responsive to the light from the light source system 104 . . . . According to some examples, the control system 106 may be configured to estimate one or more blood vessel features based on the first sensor signals. The blood vessel feature(s) may include blood vessel diameter, blood vessel distension, volumetric flow, or combinations thereof.

The sensor 205b, which is also labeled as "Sensor 2" in FIG. 2A, is an example of what may be referred to herein as a second sensor, or a second sensor system. In this example, the sensor 205b resides within the housing portion 220b on a side of the housing portion 220a that faces a person's finger when a person's finger is within the housing portion 220b. In other words, the sensor 205b resides in an inner side of the housing portion 220b.

In some examples, the sensor 205b may be, or may include, a PAPG sensor. The PAPG sensor may, in some examples, be another instance of the PAPG sensor that is described with reference to the sensor 205a. In some examples, the ultrasonic receiver system 102 of the PAPG sensor may include a sensor array, which in some examples may be a two-dimensional sensor array. However, in some examples the sensor 205b may be, or may include, another type of sensor, such as a photoplethysmography (PPG) sensor, a microphone, an accelerometer, a capacitive sensor, a radio frequency sensor, a magnetic sensor, an electrocardiogram sensor, an ultrasonic sensor, a pressure sensor, etc. According to some examples the control system 106 (not shown) may receive second sensor signals from the sensor 205b and may be configured to estimate a pulse wave velocity (PWV) based, at least in part, on signals from the sensor 205a and the sensor 205b. In some examples, the second sensor signals may be, or may include, signals from a sensor array, which in some examples may be a two-dimensional sensor array.

With the type of implementation illustrated in FIG. 2A, if the apparatus 100 is worn by an adult the sensor 205a will generally reside more than 50 millimeters from the sensor 205b. Therefore, the PWV may be considered to be a regional PWV. The control system 106 may be configured to estimate blood pressure based, at least in part, on the one or more blood vessel features and the PWV. According to some examples, the control system 106 may be configured to estimate a distance between the sensor 205a and the sensor 205b. In some such examples, the control system 106 may be configured to estimate a distance between the sensor 205a and the sensor 205b using an ultrasonic transmitter in the sensor 205a and an ultrasonic receiver in the sensor 205b, using an ultrasonic transmitter in the sensor 205b and an ultrasonic receiver in the sensor 205a, or both. By emitting ultrasonic waves at one sensor and receiving ultrasonic waves at other sensor, the control system 106 may be configured to estimate the distance between the sensor 205a and the sensor 205b by multiplying the travel time for the ultrasonic waves by the speed of sound in air.

Figure 2B:
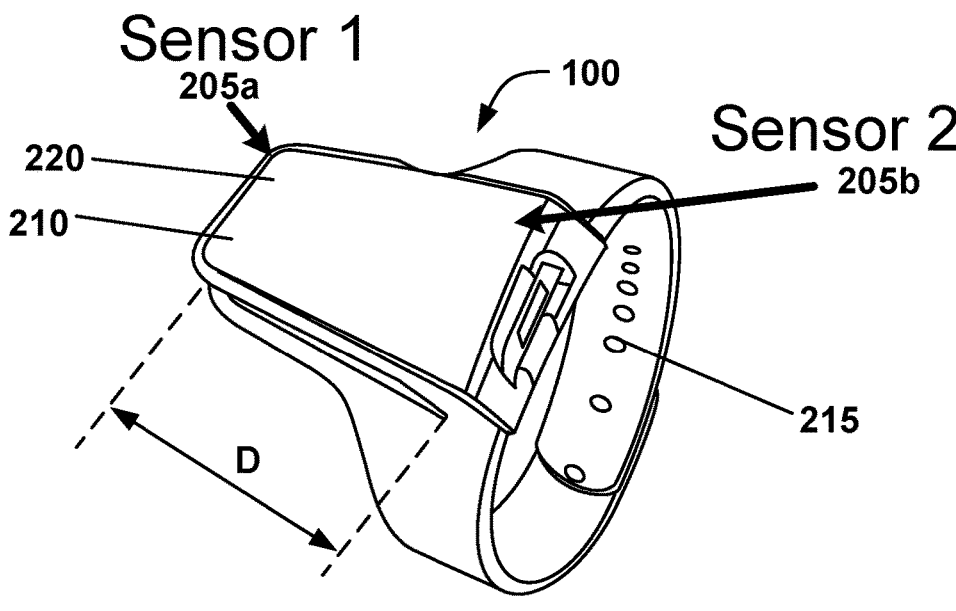
FIG. 2B shows components of an apparatus according to another example.

FIG. 2B shows components of an apparatus according to another example. As with the example shown in FIG. 2A, the apparatus 100 is configured to be worn on a person's wrist and includes an adjustable wrist band 215, a housing 220 and a display 210 that resides in or on a portion of the housing 220. However, unlike the example shown in FIG. 2A, in this example the apparatus 100 does not include apparatus portions 200a and 200b, but instead includes the sensors 205a and 205b within the housing 220. As with other disclosed examples, the types, numbers, sizes and arrangements of elements shown in FIG. 2B are merely examples.

The sensors 205a and 205b are also labeled as Sensors 1 and 2, respectively, in FIG. 2B. In this example, the sensors 205a and 205b both reside within the housing 220 on a side of the housing 220 that faces a person's wrist when the adjustable wrist band 215 is fastened to the person's wrist. In other words, the display 210 resides in or on a first side of the housing 220—which may be referred to as an outer side—and the sensors 205a and 205b reside proximate a second side of the housing 220, which may be referred to as an inner side.

In some examples, the sensor 205a may be, or may include, a PAPG sensor. According to some such examples, the sensor 205b also may be, or may include, a PAPG sensor. However, in some examples the sensor 205a, the sensor 205b, or both, may be, or may include, another type of sensor, such as an ultrasonic sensor capable of transmitting and receiving ultrasonic waves. In some examples in which the sensor 205a is, or includes, a PAPG sensor, the sensor 205a may include instances of the ultrasonic receiver system 102, the light source system 104 and the control system 106 that are described with reference to FIG. 1. Likewise, in some examples in which the sensor 205b is, or includes, a PAPG sensor, the sensor 205b may include instances of the ultrasonic receiver system 102, the light source system 104 and the control system 106 that are described with reference to FIG. 1. According to some examples, the control system 106 may be configured to control the light source system 104 to emit light towards the wrist of a person wearing the apparatus 100.

In some examples, the control system 106 may be configured to receive first sensor signals from the ultrasonic receiver system 102 of the sensor 205a, the sensor 205b, or both. The first sensor signals may be ultrasonic receiver signals corresponding to ultrasonic waves generated by a blood vessel within the person's wrist, blood within the blood vessel, or a combination thereof, responsive to the light from the light source system 104. In some alternative examples, the first sensor signals may be ultrasonic receiver signals corresponding to ultrasonic waves generated by the apparatus 100 and reflected from a blood vessel within the person's wrist, blood within the blood vessel, etc. According to some examples, the control system 106 may be configured to estimate one or more blood vessel features based on the first sensor signals. The blood vessel feature(s) may include blood vessel diameter, blood vessel distension, volumetric flow, or combinations thereof.

As noted above, in some examples the sensor 205b may be, or may include, a PAPG sensor. However, in some examples the sensor 205b may be, or may include, another type of sensor, such as a photoplethysmography (PPG) sensor, a microphone, an accelerometer, a capacitive sensor, a radio frequency sensor, a magnetic sensor, an electrocardiogram sensor, an ultrasonic sensor, a pressure sensor, etc. According to some examples the control system 106 (not shown) may receive second sensor signals from the sensor 205b and may be configured to estimate a PWV based, at least in part, on first sensor signals from the sensor 205a and second sensor signals from the sensor 205b.

With the type of implementation illustrated in FIG. 2B, the sensor 205a may or may not reside more than 50 millimeters from the sensor 205b, depending on the dimensions of the housing 220. In this example, the sensor 205a and the sensor 205b are separated by a distance D. In some examples D may be more than 50 millimeters, in which case the estimated PWV may be considered to be a regional PWV. The control system 106 may be configured to estimate blood pressure based, at least in part, on the one or more blood vessel features and the PWV. However, in other examples D may be less than 50 millimeters, in which case the estimated PWV may be considered to be a local PWV.

Figure 3A:
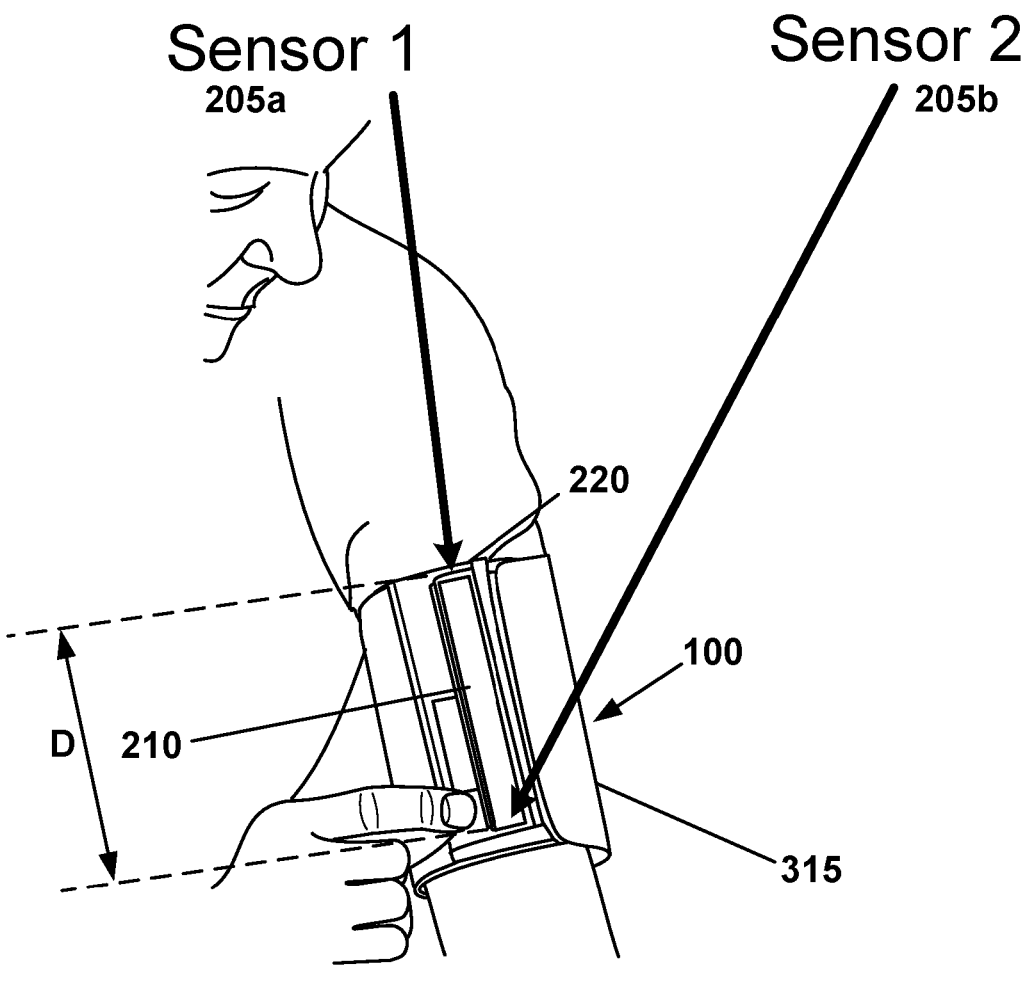
FIG. 3A shows components of an apparatus according to another example.

FIG. 3A shows components of an apparatus according to another example. As with the example shown in FIG. 2B, the sensors 205a and 205b reside within the housing 220 of the apparatus 100. The sensors 205a and 205b may, in some examples, be as described with reference to FIG. 2B. In this example, as in the example shown in FIG. 2B, the apparatus 100 also includes a display 210 that resides in or on a portion of the housing 220. However, in the example shown in FIG. 3A, the apparatus 100 is configured to be worn on a person's upper arm—in other words, above the person's elbow—instead of on a person's wrist. Accordingly, in this example the apparatus 100 includes an adjustable arm band 315. As with other disclosed examples, the types, numbers, sizes and arrangements of elements shown in FIG. 2A are merely examples.

According to some examples the control system 106 (not shown) may receive sensor signals from the sensor 205a and the sensor 205b and may be configured to estimate a PWV based, at least in part, on signals from the sensor 205a and the sensor 205b. With the type of implementation illustrated in FIG. 3A, the sensor 205a will generally reside more than 50 millimeters from the sensor 205b. In other words, D will generally be more than 50 millimeters, in which case the estimated PWV may be considered to be a regional PWV. The control system 106 may be configured to estimate blood pressure based, at least in part, on the one or more blood vessel features and the PWV. However, in other examples D may be less than 50 millimeters, in which case the estimated PWV may be considered to be a local PWV.

In some implementations, the sensor 205a may reside more than 50 millimeters from the sensor 205b, but there also may be one or more sensors residing between the sensors 205a and 205b, for example including at least a sensor 205c. The sensor 205c may be another instance of the sensor 205a or the sensor 205b. According to some such implementations, the control system 106 may be configured to estimate a regional PWV based on signals from the sensor 205a and the sensor 205b and may be configured to estimate a local PWV based on signals from the sensor 205a and the sensor 205c, on signals from the sensor 205b and the sensor 205c, or both.

Figure 3B:
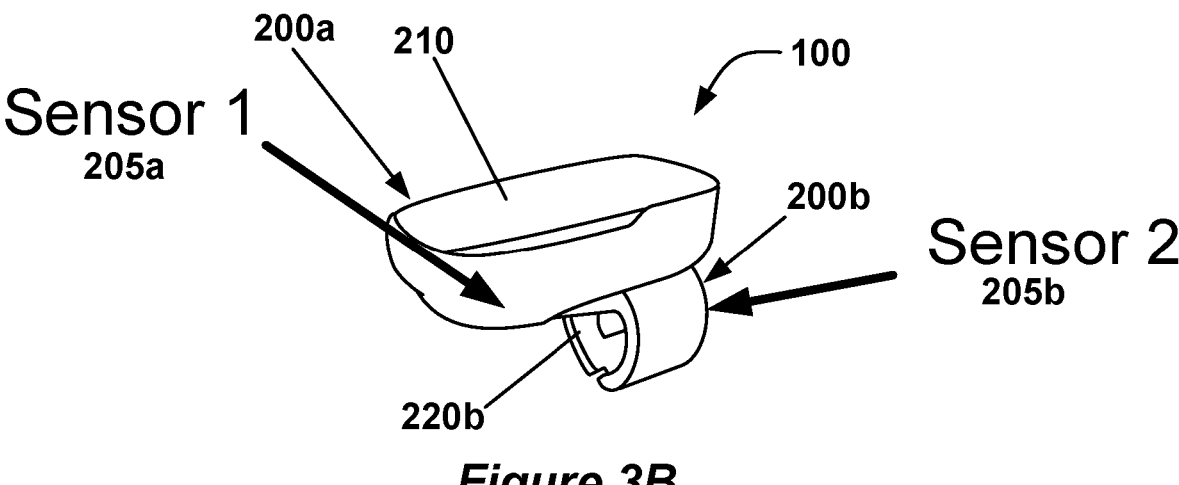
FIG. 3B shows components of an apparatus according to another example.

FIG. 3B shows components of an apparatus according to another example. As with other disclosed examples, the types, numbers, sizes and arrangements of elements shown in FIG. 3B are merely examples.

The example shown in FIG. 3B is similar in some ways to the example shown in FIG. 2A. In both examples, the apparatus 100 includes apparatus portions 200a and 200b. In both examples, the apparatus portion 200a includes a sensor 205a, a housing portion 220a and a display 210 that resides in or on a portion of the housing portion 220a. In both examples, the apparatus portion 200b is configured to be worn on a person's finger and includes a sensor 205b. In both examples, the apparatus portion 200b is electrically connected to the apparatus portion 200a. The sensors 205a and 205b shown in FIG. 3B may, in some examples, be as described with reference to FIG. 2A.

However, in the example shown in FIG. 3B, the electrical interface is not a wire or a cable, as shown in the example of FIG. 2A. According to the example shown in FIG. 3B, the apparatus portions 200a and 200b, as well as the housing portion 220a and the housing portion 220b, are physically and electrically coupled to one another. Therefore, both of the apparatus portions 200a and 200b are configured to be worn on a person's finger.

The example shown in FIG. 3B has some potential advantages relative to the example of FIG. 2A. One such potential advantage is that in the example shown in FIG. 3B, the relative positions of the sensors 205a and 205b are both fixed and known, whereas in the example shown in FIG. 2A the relative positions of the sensors 205a and 205b are not fixed and may be challenging to determine with accuracy.

According to some examples the control system 106 (not shown) may receive sensor signals from the sensor 205a and the sensor 205b and may be configured to estimate a PWV based, at least in part, on signals from the sensor 205a and the sensor 205b. With the type of implementation illustrated in FIG. 3B, the sensor 205a will generally reside less than 50 millimeters from the sensor 205b, in which case the estimated PWV may be considered to be a local PWV. However, in other examples the sensor 205a will reside more than 50 millimeters from the sensor 205b, in which case the estimated PWV may be considered to be a regional PWV. The control system 106 may be configured to estimate blood pressure based, at least in part, on the one or more blood vessel features and the PWV.

Figure 4A:
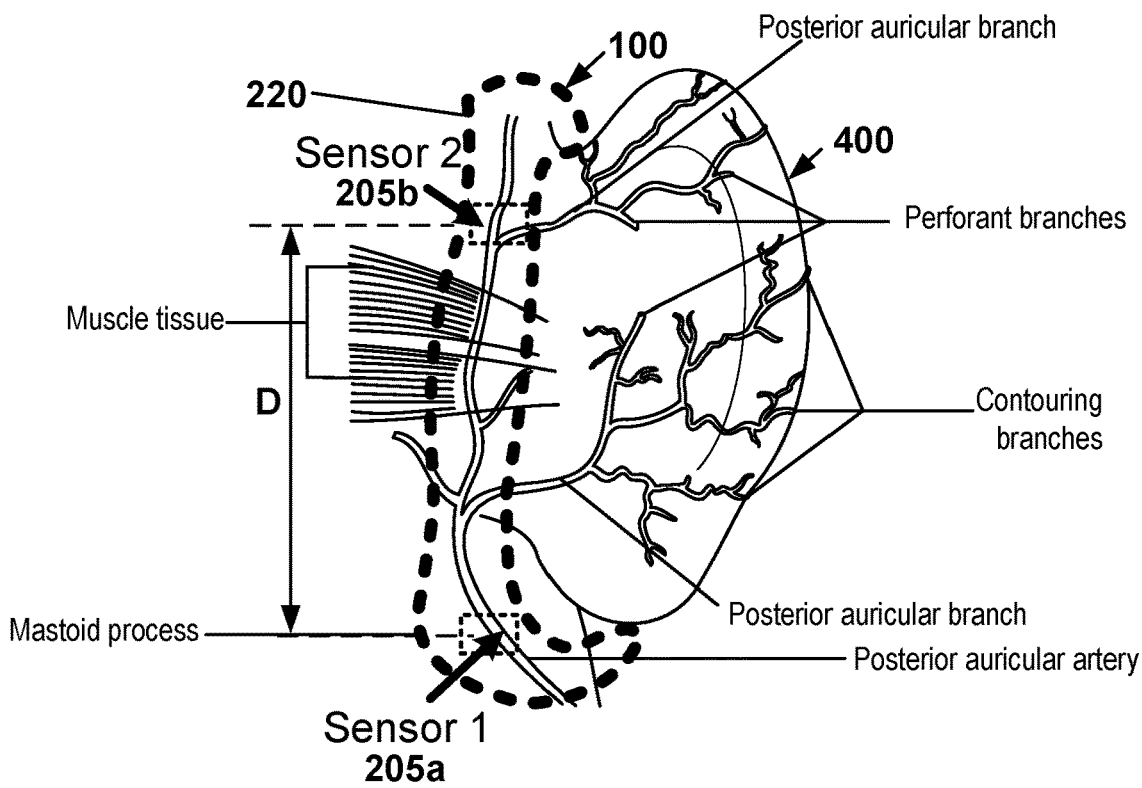
FIGS. 4A and 4B show alternative apparatus examples.
Figure 4B:
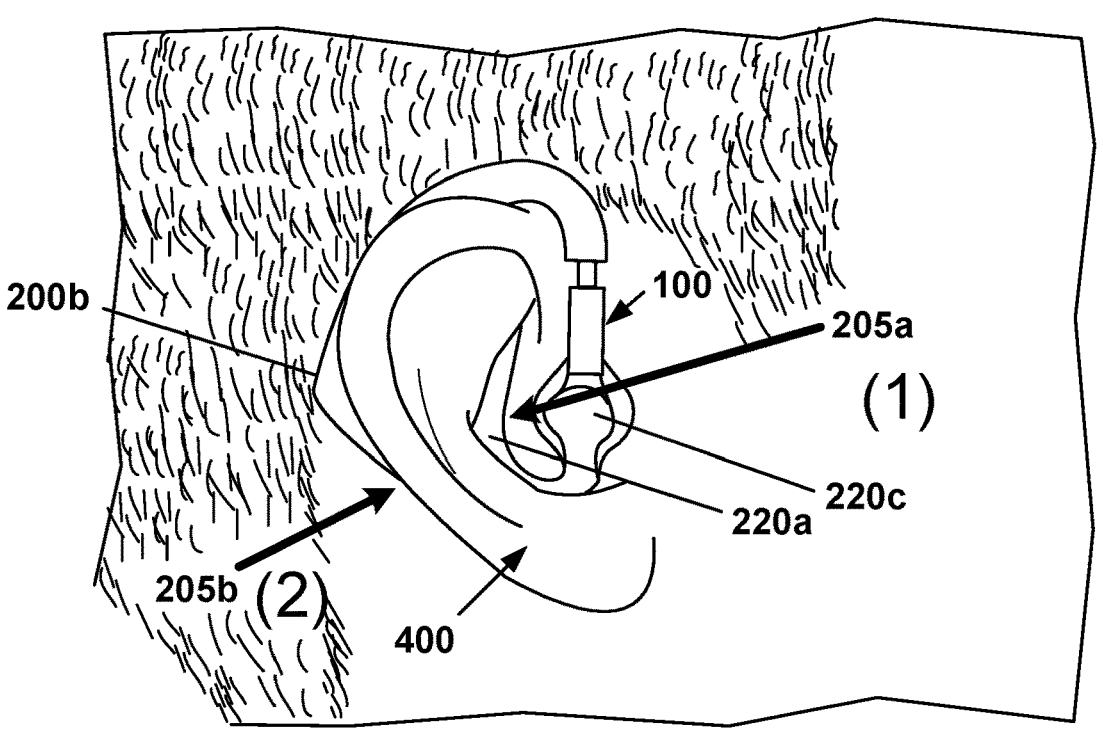

FIGS. 4A and 4B show alternative apparatus examples. In these examples, the apparatus 100 is configured to be worn in a human ear, on a human ear, or both. As with other disclosed examples, the types, numbers, sizes and arrangements of elements shown in FIGS. 4A and 4B are merely examples.

FIG. 4A shows examples of bone, muscles and blood vessels in and near the back of a human ear 400, including the mastoid process, muscle tissue attached to the mastoid process, muscle tissue attached to the posterior area of the ear 400, the posterior auricular artery, and branches thereof. In the example shown in FIG. 4A, the sensors 205a and 205b reside within the housing 220 in positions such that, when the apparatus 100 is worn in the ear 400, both of the sensors 205a and 205b are positioned on the posterior auricular artery.

According to some examples the control system 106 (not shown) may receive sensor signals from the sensor 205a and the sensor 205b and may be configured to estimate a PWV based, at least in part, on signals from the sensor 205a and the sensor 205b. When the type of implementation illustrated in FIG. 4A is worn by an adult, the sensor 205a will generally reside more than 50 millimeters from the sensor 205b, in which case the estimated PWV may be considered to be a regional PWV. However, in other examples—such as when the type of implementation illustrated in FIG. 4A is worn by a child—the sensor 205a will reside less than 50 millimeters from the sensor 205b, in which case the estimated PWV may be considered to be a local PWV. The control system 106 may be configured to estimate blood pressure based, at least in part, on the one or more blood vessel features and the PWV.

FIG. 4B shows an alternative example of an apparatus 100 that is configured to be worn on, and in, the ear 400. In this example, the sensor 205a resides in the housing portion 220a, which is configured to reside proximate, or within, an ear concha. According to this example, the sensor 205b resides in the housing portion 220b, which is configured to wrap around the outside of the ear 400. In this example, the housing portions 220a and 220b are configured to position the sensors 205a and 205b such that the sensors 205a and 205b are on opposite sides of the same volume of the ear 400. According to this example, the housing portion 220c is configured to be inserted into an ear canal of the ear 400.

According to some examples the control system 106 (not shown) may receive sensor signals from the sensor 205a and the sensor 205b and may be configured to estimate a PWV based, at least in part, on signals from the sensor 205a and the sensor 205b. The control system 106 may be configured to estimate blood pressure based, at least in part, on the one or more blood vessel features and the PWV.

In some examples, the apparatus 100 shown in FIG. 4A, the apparatus 100 shown in FIG. 4B, or both, also may include at least one loudspeaker. The at least one loudspeaker may, for example, reside in the housing portion 220c. In some such examples, the control system (not shown) may be configured to control the at least one loudspeaker to play back audio content. According to some examples, the apparatus 100 shown in FIGS. 4A and 4B also may include at least one microphone. In some such examples, the control system (not shown) may be configured to control the at least one loudspeaker to provide hearing aid functionality that is based, at least in part, in microphone signals received from the at least one microphone.

Figure 5A:
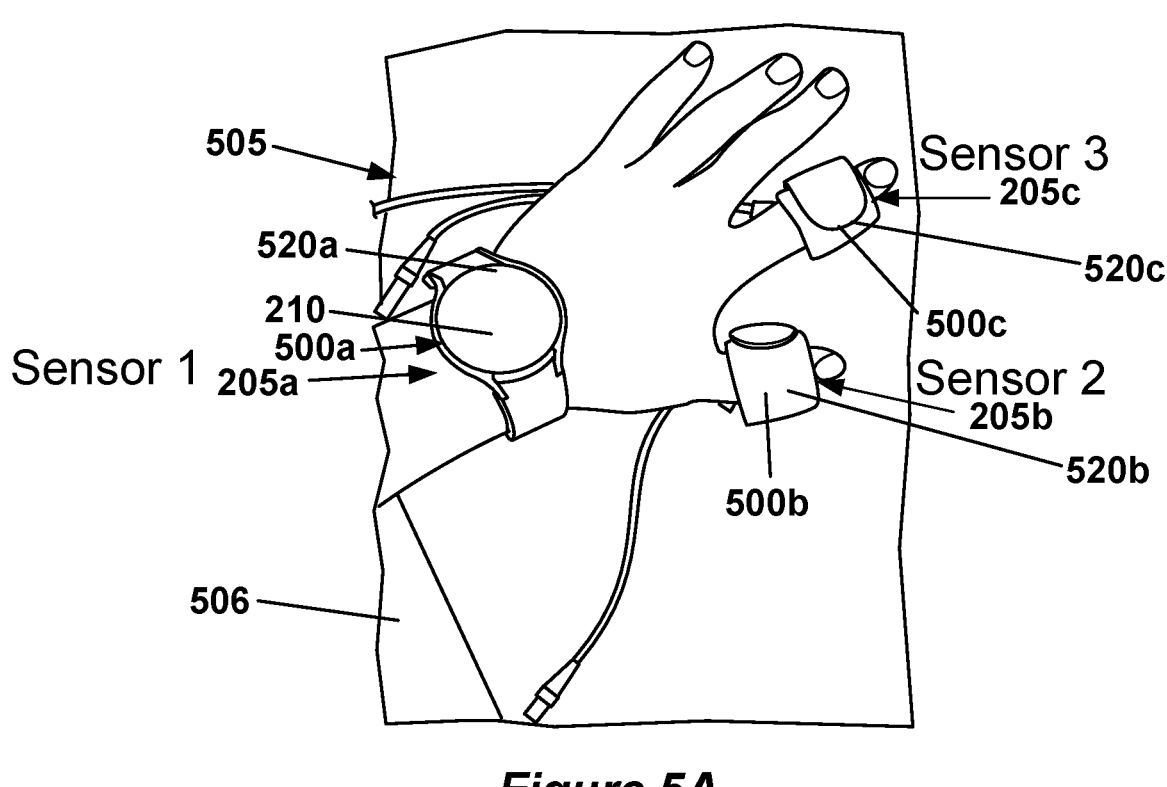
FIGS. 5A and 5B show alternative examples.
Figure 5B:
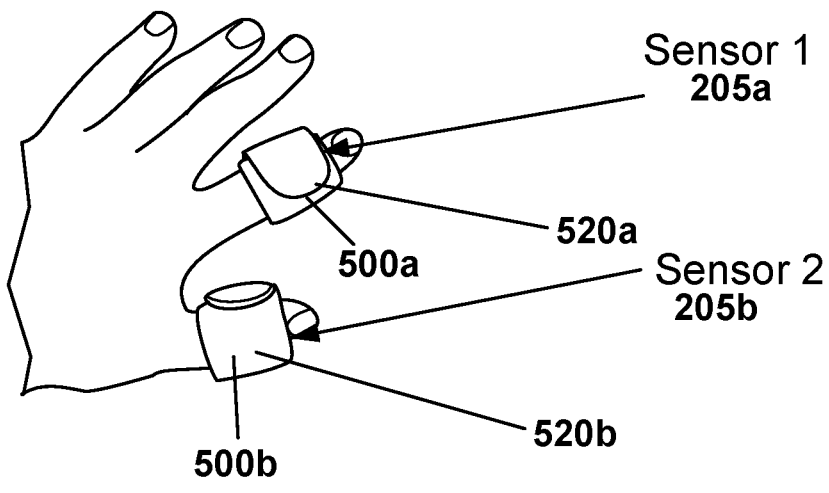

FIGS. 5A and 5B show alternative examples. In these examples, the system 505 includes devices that are configured to be worn on a human finger. As with other disclosed examples, the types, numbers, sizes and arrangements of elements shown in FIGS. 5A and 5B are merely examples.

According to the examples shown in FIGS. 5A and 5B, the apparatus 500a includes Sensor 1, which is also referred to as sensor 205a. In the examples shown in FIGS. 5A and 5B, the apparatus 500a is an instance of the apparatus 100 of FIG. 1 and is PAPG-capable. However, as described with reference to FIG. 2A and elsewhere herein, in some alternative examples the sensor 205a may be, or may include, another type of sensor.

In the example shown in FIG. 5A, the apparatus 500a is a smart watch. Here, the apparatus 500b and the apparatus 500c are both configured to be worn on a human finger. In this example, the sensor 205b resides in the housing 520b and the sensor 205c resides in the housing 520c.

One may observe that the implementation shown in FIG. 5A is similar to that shown in FIG. 2A. The sensors 205b and 205c of FIG. 5A may be instances of the sensor 205b that is described with reference to FIG. 2A. However, in the example shown in FIG. 5A, the apparatus 500b and the apparatus 500c are both configured for electrical connectivity with the control system 506. In this example, the control system 106 (not shown) of the apparatus 500a is configured for wireless communication with the control system 506. Accordingly, the control system 106 may receive signals from the sensors 205b and 205c via the control system 506. In some examples, the control system 106 or the control system 506 may be configured to estimate PWV, blood pressure, etc., based on signals from the sensors 205a and 205b, based on signals from the sensors 205a and 205c, or based on signals from the sensors 205a, 205b and 205c.

In the example shown in FIG. 5B, both the apparatus 500a and the apparatus 500b are configured to be worn on a human finger. In this example, the sensor 205a resides in the housing 520a and the sensor 205b resides in the housing 520b. In this example, the control system 106 (not shown) of the apparatus 500a is configured for wireless communication with the apparatus 500b. In some examples, the control system 106 may be configured to estimate PWV, blood pressure, etc., based on signals from the sensors 205a and 205b.

Figure 6:
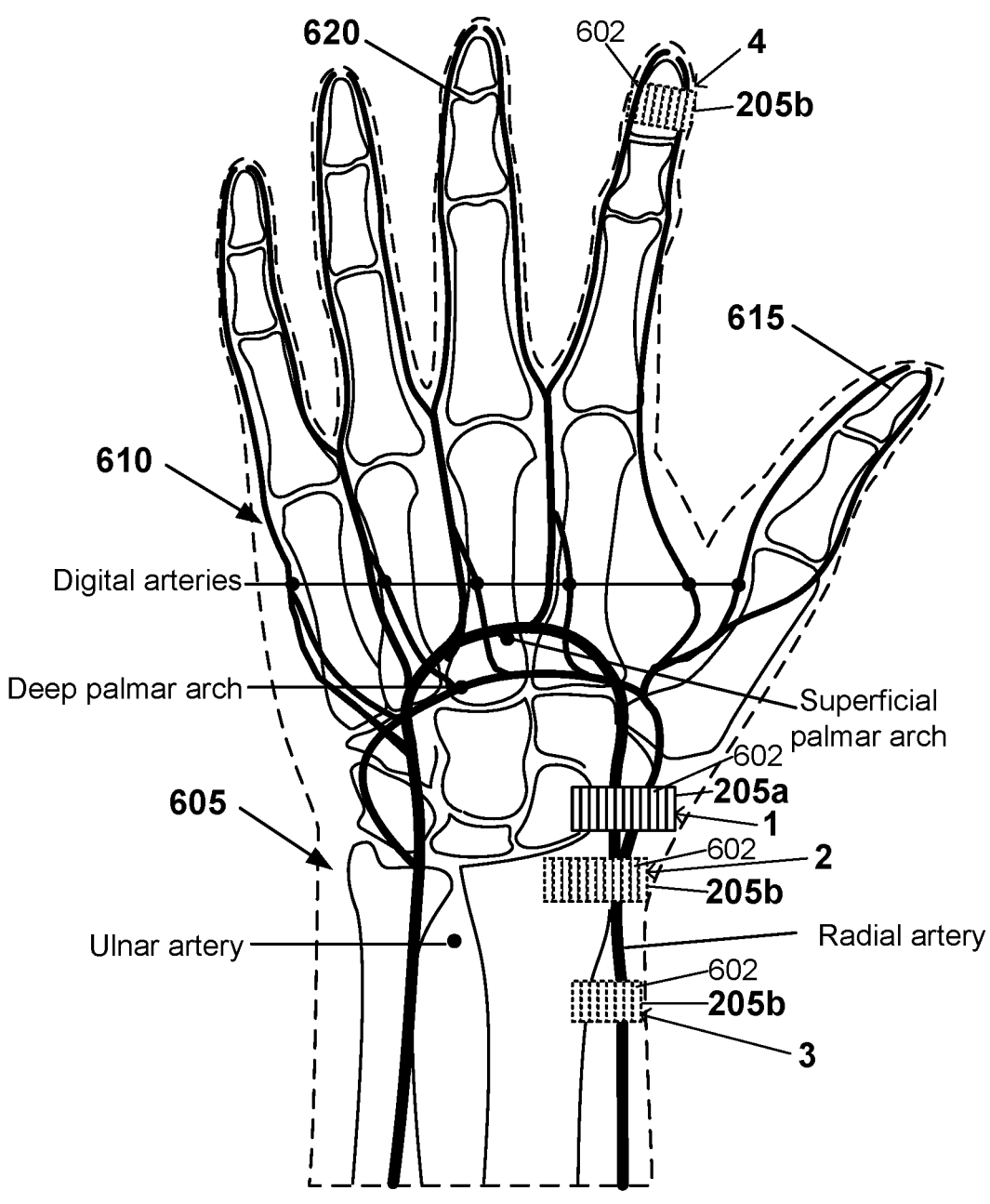
FIG. 6 shows examples of possible sensor locations on a human wrist and finger.

FIG. 6 shows examples of possible sensor locations on a human wrist and finger. As with other disclosed examples, the types, numbers, sizes and arrangements of elements that are described with reference to FIG. 6 are merely examples.

FIG. 6 shows examples of bones and arteries in a wrist and hand, with 3 of the 4 possible sensor locations corresponding to positions along the radial artery. In some alternative examples, 2 or more sensor locations may correspond to positions along another artery, such as the ulnar artery.

According to some examples, an instance of the sensor 205a may be positioned at location 1 and an instance of the sensor 205b may be positioned at location 2, location 3 or location 4. The sensors 205a and 205b may be as described with reference to FIG. 2A. In some such examples, at least the sensor 205a is, or includes, a PAPG sensor. However, in some examples the sensor 205a may be, or may include, one of the other types of sensors disclosed herein. According to this example, the sensor 205a includes an array of sensor elements 602, which in this instance are, or include, ultrasonic receiver elements of an ultrasonic receiver system 102. In this example—as suggested by the dashed outlines—the sensor 205b also may include an array of sensor elements 602. The type of sensor elements 602 will depend in the particular implementation(s) of the sensor 205b. Although the arrays of sensor elements 602 shown in FIG. 6 are linear arrays, in some examples the arrays of sensor elements 602 may be two-dimensional arrays. Arrays of sensor elements have the potential advantage—as compared to individual sensors—of being able to more clearly identify the position of a blood vessel, such as the radial artery. However, according to some alternative examples, the sensor 205a, the sensor 205b, or both, may be individual sensors.

In some alternative examples, an instance of the sensor 205a may be positioned at location 1, location 2 or location 3. In some such examples, an instance of the sensor 205b may be positioned at one or more of the other 3 locations. According to some such examples, an instance of the sensor 205b may be positioned at two of the other 3 locations or at all 3 of the other 3 locations.

In some examples, the sensor(s) at location 1, location 2, location 3, or combinations thereof, may reside in a single apparatus that is configured to be attached to the wrist 605, such as a smart watch, a health monitoring device with a wrist band, etc. In this example, if a sensor resides at location 4, the sensor will reside in an apparatus that is configured to be attached to a human finger. In some alternative implementations, location 4 may be at a corresponding position of another digit of the hand 610, such as the thumb 615, the middle finger 620, etc.

FIG. 7 is a flow diagram that shows examples of some disclosed operations. The blocks of FIG. 7 may, for example, be performed by the apparatus 100 of FIG. 1 or by a similar apparatus. As with other methods disclosed herein, the method outlined in FIG. 7 may include more or fewer blocks than indicated. Moreover, the blocks of methods disclosed herein are not necessarily performed in the order indicated. In some instances, one or more of the blocks shown in FIG. 7 may be performed concurrently.

In this example, block 705 involves receiving first sensor signals from at least a first ultrasonic sensor of an ultrasonic receiver system. In this example, the first sensor signals include ultrasonic receiver signals corresponding to ultrasonic waves generated by a target object responsive to light from a light source system. The target object may be a finger, a wrist, etc., depending on the particular example. The first sensor signals may, in some examples, be received from an instance of the sensor 205a that is disclosed herein.

According to this example, block 710 involves estimating one or more blood vessel features based on the first ultrasonic receiver signals. The one or more blood vessel features may include blood vessel diameter, blood vessel distension, volumetric flow, or combinations thereof.

According to this example, block 715 involves receiving second sensor signals from a second sensor. The second sensor signals may, in some examples, be received from an instance of the sensor 205b that is disclosed herein.

In this example, block 720 involves estimating a pulse wave velocity based, at least in part, on the first ultrasonic receiver signals and the second sensor signals. According to this example, block 725 involves estimating blood pressure based, at least in part, on the one or more blood vessel features and the pulse wave velocity.

According to some examples, the second sensor signals may be received from a second device. However, in some examples, the second sensor signals may be received from a second sensor of the same device that includes the ultrasonic receiver system. In some examples, the second sensor signals may be signals from a photoplethysmography sensor, signals from a PAPG sensor, microphone signals, signals from an accelerometer, capacitive sensor signals, signals from a radio frequency sensor, signals from a magnetic sensor, electrocardiogram signals, signals from an ultrasonic sensor, signals from a pressure sensor, signals from a camera, or combinations thereof.

In some examples, the first sensor signals may correspond to ultrasonic waves generated within a person's wrist. In some such examples, the second sensor signals may be obtained from the person's finger. In some alternative examples, the second sensor signals may be obtained from the person's arm.

According to some examples, method 700 may involve estimating a distance between the first ultrasonic sensor and the second sensor. However, in some examples the distance between the first ultrasonic sensor and the second sensor may be known. In some such examples, a single device may include the first ultrasonic sensor and the second sensor.

In some examples, the first sensor signals, the second sensor signals, or both, may include signals from a sensor array. According to some examples, the sensor array may be a two-dimensional sensor array. According to some examples, method 700 may involve extracting and evaluating heart rate waveform (HRW) features.

Figure 8:
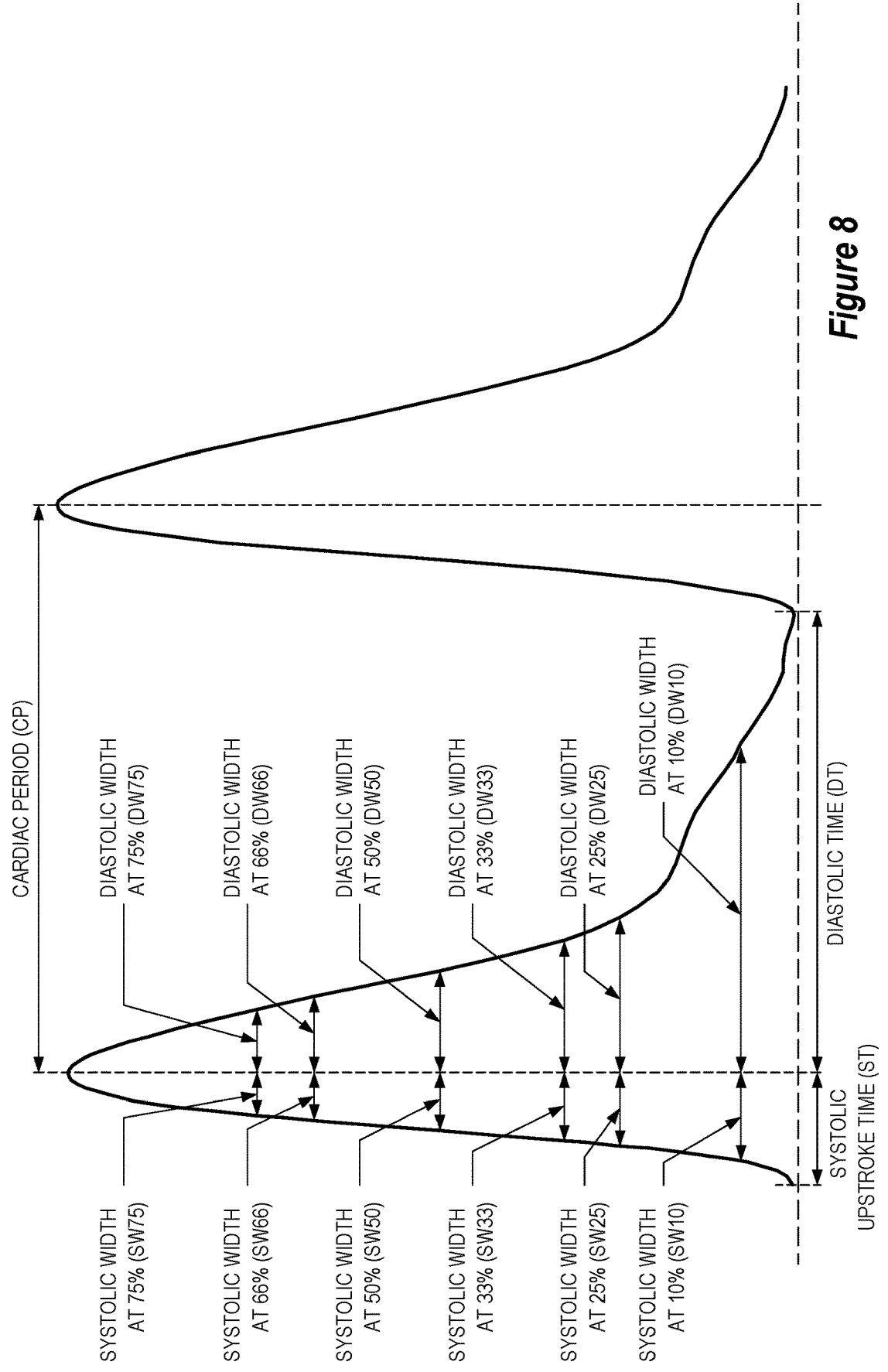
FIG. 8 shows examples of heart rate waveform (HRW) features that may be extracted according to some implementations of the method of FIG. 7.
Figure 10:
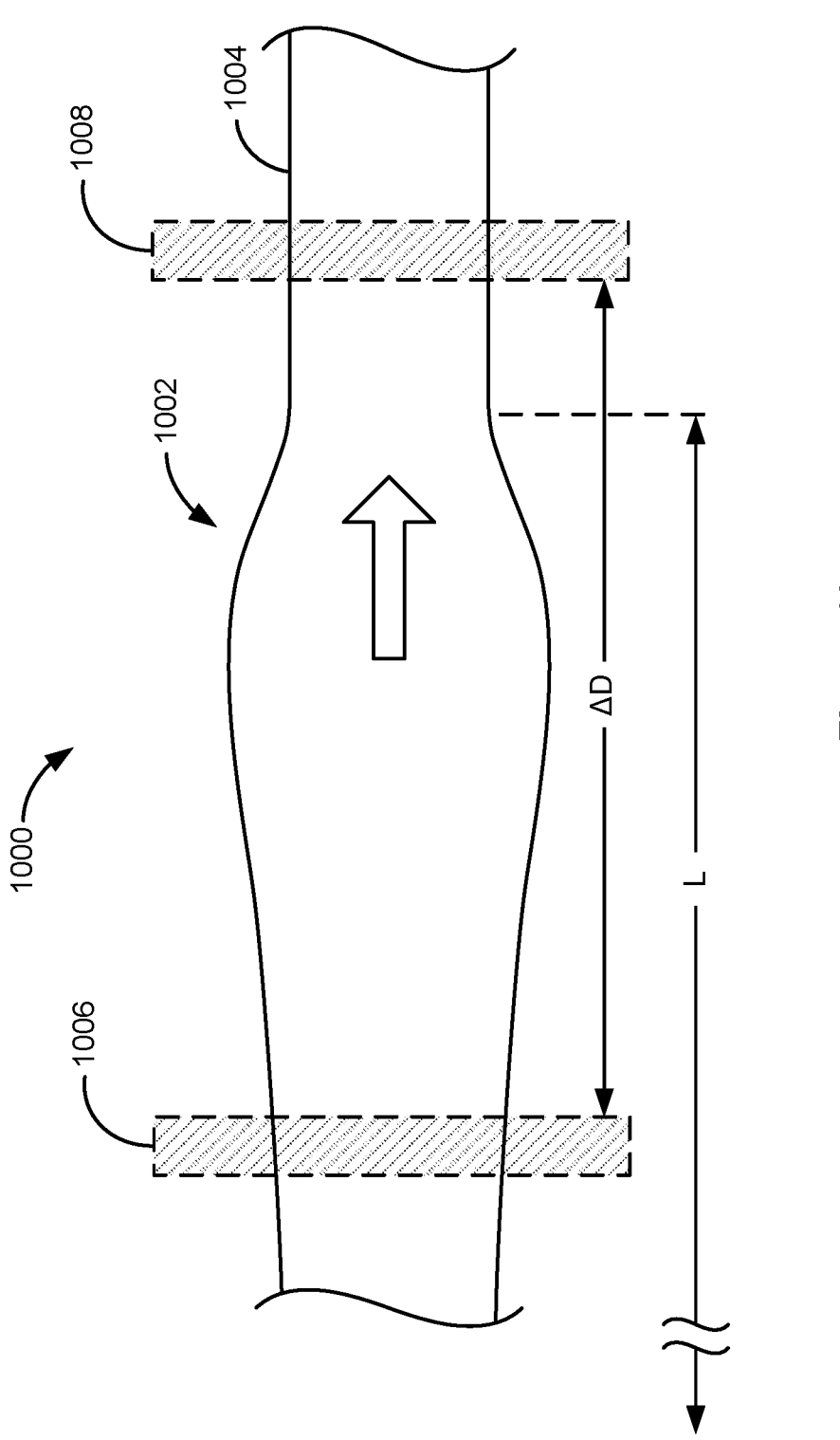
FIG. 10 shows a cross-sectional side view of a diagrammatic representation of a portion of an artery through which a pulse is propagating.

FIG. 8 shows examples of heart rate waveform (HRW) features that may be extracted according to some implementations of the method of FIG. 10. The horizontal axis of FIG. 8 represents time and the vertical axis represents signal amplitude. The cardiac period is indicated by the time between adjacent peaks of the HRW. The systolic and diastolic time intervals are indicated below the horizontal axis. During the systolic phase of the cardiac cycle, as a pulse propagates through a particular location along an artery, the arterial walls expand according to the pulse waveform and the elastic properties of the arterial walls. Along with the expansion is a corresponding increase in the volume of blood at the particular location or region, and with the increase in volume of blood an associated change in one or more characteristics in the region. Conversely, during the diastolic phase of the cardiac cycle, the blood pressure in the arteries decreases and the arterial walls contract. Along with the contraction is a corresponding decrease in the volume of blood at the particular location, and with the decrease in volume of blood an associated change in the one or more characteristics in the region.

The HRW features that are illustrated in FIG. 8 pertain to the width of the systolic and/or diastolic portions of the HRW curve at various "heights," which are indicated by a percentage of the maximum amplitude. For example, the SW50 feature is the width of the systolic portion of the HRW curve at a "height" of 50% of the maximum amplitude. In some implementations, the HRW features used for blood pressure estimation may include some or all of the SW10, SW25, SW33, SW50, SW66, SW75, DW10, DW25, DW33, DW50, DW66 and DW75 HRW features. In other implementations, additional HRW features may be used for blood pressure estimation. Such additional HRW features may, in some instances, include the sum and ratio of the SW and DW at one or more "heights," e.g., (DW75+SW75), DW75/SW75, (DW66+SW66), DW66/SW66, (DW50+SW50), DW50/SW50, (DW33+SW33), DW33/SW33, (DW25+SW25), DW25/SW25 and/or (DW10+SW10), DW10/SW10. Other implementations may use yet other HRW features for blood pressure estimation. Such additional HRW features may, in some instances, include sums, differences, ratios and/or other operations based on more than one "height," such as (DW75+SW75)/(DW50+SW50), (DW50+SW50/(DW10+SW10), etc.

Figure 9:
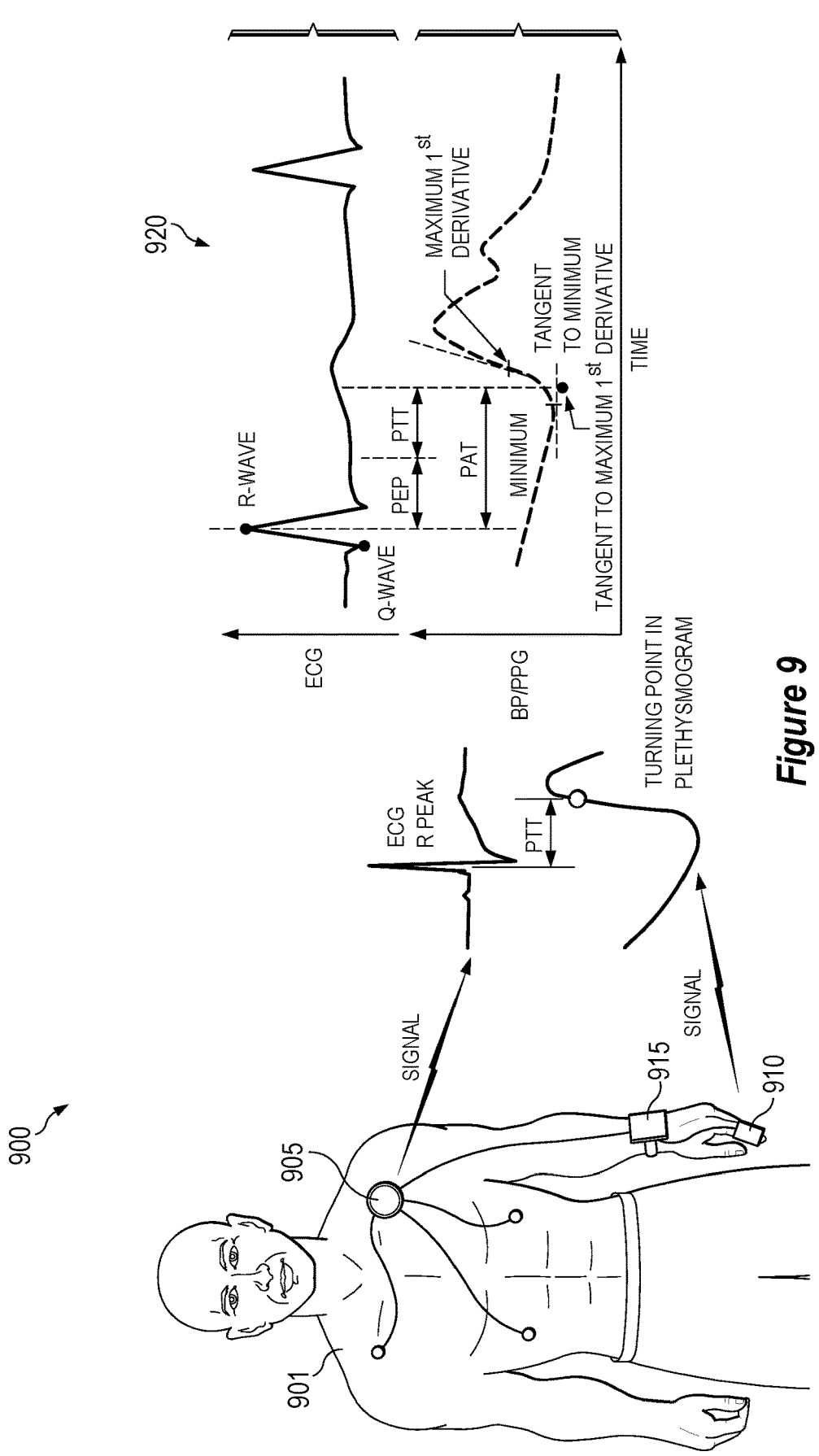
FIG. 9 shows examples of devices that may be used in a system for estimating blood pressure based, at least in part, on pulse transit time (PTT).

FIG. 9 shows examples of devices that may be used in a system for estimating blood pressure based, at least in part, on pulse transit time (PTT). As with other figures provided herein, the numbers, types and arrangements of elements are merely presented by way of example. According to this example, the system 900 includes at least two sensors. In this example, the system 900 includes at least an electrocardiogram sensor 905 and a device 910 that is configured to be mounted on a finger of the person 901. In this example, the device 910 is, or includes, an apparatus configured to perform at least some PAPG methods disclosed herein. For example, the device 910 may be, or may include, the apparatus 300 of FIG. 3 or a similar apparatus.

As noted in the graph 920, the PAT includes two components, the pre-ejection period (PEP, the time needed to convert the electrical signal into a mechanical pumping force and isovolumetric contraction to open the aortic valves) and the PTT. The starting time for the PAT can be estimated based on the QRS complex—an electrical signal characteristic of the electrical stimulation of the heart ventricles. As shown by the graph 920, in this example the beginning of a pulse arrival time (PAT) may be calculated according to an R-Wave peak measured by the electrocardiogram sensor 905 and the end of the PAT may be detected via analysis of signals provided by the device 910. In this example, the end of the PAT is assumed to correspond with an intersection between a tangent to a local minimum value detected by the device 910 and a tangent to a maximum slope/first derivative of the sensor signals after the time of the minimum value.

There are many known algorithms for blood pressure estimation based on the PTT and/or the PAT, some of which are summarized in Table 1 and described in the corresponding text on pages 5-10 of Sharma, M., et al., *Cuff-Less and Continuous Blood Pressure Monitoring: a Methodological Review* ("Sharma"), in Multidisciplinary Digital Publishing Institute (MDPI) Technologies 2017, 5, 21, both of which are hereby incorporated by reference.

Some previously-disclosed methods have involved calculating blood pressure according to one or more of the equations shown in Table 1 of Sharma, or other known equations, based on a PTT and/or PAT measured by a sensor system that includes a PPG sensor. As noted above, some disclosed PAPG-based implementations are configured to distinguish artery HRWs from other HRWs. Such implementations may provide more accurate measurements of the PTT and/or PAT, relative to those measured by a PPG sensor. Therefore, disclosed PAPG-based implementations may provide more accurate blood pressure estimations, even when the blood pressure estimations are based on previously-known formulae.

Other implementations of the system 900 may not include the electrocardiogram sensor 905. In some such implementations, the device 915, which is configured to be mounted on a wrist of the person 901, may be, or may include, an apparatus configured to perform at least some PAPG methods disclosed herein. For example, the device 915 may be, or may include, the apparatus 200 of FIG. 2 or a similar apparatus. According to some such examples, the device 915 may include a light source system and two or more ultrasonic receivers. One example is described below with reference to FIG. 11A. In some examples, the device 915 may include an array of ultrasonic receivers.

In some implementations of the system 900 that do not include the electrocardiogram sensor 905, the device 910 may include a light source system and two or more ultrasonic receivers. One example is described below with reference to FIG. 11B.

FIG. 10 shows a cross-sectional side view of a diagrammatic representation of a portion of an artery 1000 through which a pulse 1002 is propagating. The block arrow in FIG. 10 shows the direction of blood flow and pulse propagation. As diagrammatically shown, the propagating pulse 1002 causes strain in the arterial walls 1004, which is manifested in the form of an enlargement in the diameter (and consequently the cross-sectional area) of the arterial walls—referred to as "distension." The spatial length L of an actual propagating pulse along an artery (along the direction of blood flow) is typically comparable to the length of a limb, such as the distance from a subject's shoulder to the subject's wrist or finger, and is generally less than one meter (m). However, the length L of a propagating pulse can vary considerably from subject to subject, and for a given subject, can vary significantly over durations of time depending on various factors. The spatial length L of a pulse will generally decrease with increasing distance from the heart until the pulse reaches capillaries.

As described above, some particular implementations relate to devices, systems and methods for estimating blood pressure or other cardiovascular characteristics based on estimates of an arterial distension waveform. The terms "estimating," "measuring," "calculating," "inferring," "deducing," "evaluating," "determining" and "monitoring" may be used interchangeably herein where appropriate unless otherwise indicated. Similarly, derivations from the roots of these terms also are used interchangeably where appropriate; for example, the terms "estimate," "measurement," "calculation," "inference" and "determination" also are used interchangeably herein. In some implementations, the pulse wave velocity (PWV) of a propagating pulse may be estimated by measuring the pulse transit time (PTT) of the pulse as it propagates from a first physical location along an artery to another more distal second physical location along the artery. It will be appreciated that this PTT is different from the PTT that is described above with reference to FIG. 15. However, either version of the PTT may be used for the purpose of blood pressure estimation. Assuming that the physical distance $\Delta D$ between the first and the second physical locations is ascertainable, the PWV can be estimated as the quotient of the physical spatial distance $\Delta D$ traveled by the pulse divided by the time (PTT) the pulse takes in traversing the physical spatial distance $\Delta D$. Generally, a first sensor positioned at the first physical location is used to determine a starting time (also referred to herein as a "first temporal location") at which point the pulse arrives at or propagates through the first physical location. A second sensor at the second physical location is used to determine an ending time (also referred to herein as a "second temporal location") at which point the pulse arrives at or propagates through the second physical location and continues through the remainder of the arterial branch. In such examples, the PTT represents the temporal distance (or time difference) between the first and the second temporal locations (the starting and the ending times).

The fact that measurements of the arterial distension waveform are performed at two different physical locations implies that the estimated PWV inevitably represents an average over the entire path distance $\Delta D$ through which the pulse propagates between the first physical location and the second physical location. More specifically, the PWV generally depends on a number of factors including the density of the blood $\rho$, the stiffness E of the arterial wall (or inversely the elasticity), the arterial diameter, the thickness of the arterial wall, and the blood pressure. Because both the arterial wall elasticity and baseline resting diameter (for example, the diameter at the end of the ventricular diastole period) vary significantly throughout the arterial system, PWV estimates obtained from PTT measurements are inherently average values (averaged over the entire path length $\Delta D$ between the two locations where the measurements are performed).

In traditional methods for obtaining PWV, the starting time of the pulse has been obtained at the heart using an electrocardiogram (ECG) sensor, which detects electrical signals from the heart. For example, the starting time can be estimated based on the QRS complex—an electrical signal characteristic of the electrical stimulation of the heart ventricles. In such approaches, the ending time of the pulse is typically obtained using a different sensor positioned at a second location (for example, a finger). As a person having ordinary skill in the art will appreciate, there are numerous arterial discontinuities, branches, and variations along the entire path length from the heart to the finger. The PWV can change by as much as or more than an order of magnitude along various stretches of the entire path length from the heart to the finger. As such, PWV estimates based on such long path lengths are unreliable.

In various implementations described herein, PTT estimates are obtained based on measurements (also referred to as "arterial distension data" or more generally as "sensor data") associated with an arterial distension signal obtained by each of a first arterial distension sensor 1006 and a second arterial distension sensor 1008 proximate first and second physical locations, respectively, along an artery of interest. In some particular implementations, the first arterial distension sensor 1006 and the second arterial distension sensor 1008 are advantageously positioned proximate first and second physical locations between which arterial properties of the artery of interest, such as wall elasticity and diameter, can be considered or assumed to be relatively constant. In this way, the PWV calculated based on the PTT estimate is more representative of the actual PWV along the particular segment of the artery. In turn, the blood pressure P estimated based on the PWV is more representative of the true blood pressure. In some implementations, the magnitude of the distance $\Delta D$ of separation between the first arterial distension sensor 1006 and the second arterial distension sensor 1008 (and consequently the distance between the first and the second locations along the artery) can be in the range of about 1 centimeter (cm) to tens of centimeters—long enough to distinguish the arrival of the pulse at the first physical location from the arrival of the pulse at the second physical location, but close enough to provide sufficient assurance of arterial consistency. In some specific implementations, the distance $\Delta D$ between the first and the second arterial distension sensors 1006 and 1008 can be in the range of about 1 cm to about 30 cm, and in some implementations, less than or equal to about 20 cm, and in some implementations, less than or equal to about 10 cm, and in some specific implementations less than or equal to about 5 cm. In some other implementations, the distance $\Delta D$ between the first and the second arterial distension sensors 1006 and 1008 can be less than or equal to 1 cm, for example, about 0.1 cm, about 0.25 cm, about 0.5 cm or about 0.75 cm. By way of reference, a typical PWV can be about 15 meters per second (m/s). Using an ambulatory monitoring device in which the first and the second arterial distension sensors 1006 and 1008 are separated by a distance of about 5 cm, and assuming a PWV of about 15 m/s implies a PTT of approximately 3.3 milliseconds (ms).

The value of the magnitude of the distance $\Delta D$ between the first and the second arterial distension sensors 1006 and 1008, respectively, can be preprogrammed into a memory within a monitoring device that incorporates the sensors (for example, such as a memory of, or a memory configured for communication with, the control system 306 that is described above with reference to FIG. 3). As will be appreciated by a person of ordinary skill in the art, the spatial length L of a pulse can be greater than the distance $\Delta D$ from the first arterial distension sensor 1006 to the second arterial distension sensor 1008 in such implementations. As such, although the diagrammatic pulse 1002 shown in FIG. 10 is shown as having a spatial length L comparable to the distance between the first arterial distension sensor 1006 and the second arterial distension sensor 1008, in actuality each pulse can typically have a spatial length L that is greater and even much greater than (for example, about an order of magnitude or more than) the distance $\Delta D$ between the first and the second arterial distension sensors 1006 and 1008.

Sensing Architecture and Topology

In some implementations of the ambulatory monitoring devices disclosed herein, both the first arterial distension sensor 1006 and the second arterial distension sensor 1008 are sensors of the same sensor type. In some such implementations, the first arterial distension sensor 1006 and the second arterial distension sensor 1008 are identical sensors. In such implementations, each of the first arterial distension sensor 1006 and the second arterial distension sensor 1008 utilizes the same sensor technology with the same sensitivity to the arterial distension signal caused by the propagating pulses, and has the same time delays and sampling characteristics. In some implementations, each of the first arterial distension sensor 1006 and the second arterial distension sensor 1008 is configured for photoacoustic plethysmography (PAPG) sensing, e.g., as disclosed elsewhere herein. Some such implementations include a light source system and two or more ultrasonic receivers, which may be instances of the light source system 104 and the receiver system 102 of FIG. 1. In some implementations, each of the first arterial distension sensor 1006 and the second arterial distension sensor 1008 is configured for ultrasound sensing via the transmission of ultrasonic signals and the receipt of corresponding reflections. In some alternative implementations, each of the first arterial distension sensor 1006 and the second arterial distension sensor 1008 may be configured for impedance plethysmography (IPG) sensing, also referred to in biomedical contexts as bioimpedance sensing. In various implementations, whatever types of sensors are utilized, each of the first and the second arterial distension sensors 1006 and 1008 broadly functions to capture and provide arterial distension data indicative of an arterial distension signal resulting from the propagation of pulses through a portion of the artery proximate to which the respective sensor is positioned. For example, the arterial distension data can be provided from the sensor to a processor in the form of voltage signal generated or received by the sensor based on an ultrasonic signal or an impedance signal sensed by the respective sensor.

As described above, during the systolic phase of the cardiac cycle, as a pulse propagates through a particular location along an artery, the arterial walls expand according to the pulse waveform and the elastic properties of the arterial walls. Along with the expansion is a corresponding increase in the volume of blood at the particular location or region, and with the increase in volume of blood an associated change in one or more characteristics in the region. Conversely, during the diastolic phase of the cardiac cycle, the blood pressure in the arteries decreases and the arterial walls contract. Along with the contraction is a corresponding decrease in the volume of blood at the particular location, and with the decrease in volume of blood an associated change in the one or more characteristics in the region.

In the context of bioimpedance sensing (or impedance plethysmography), the blood in the arteries has a greater electrical conductivity than that of the surrounding or adjacent skin, muscle, fat, tendons, ligaments, bone, lymph or other tissues. The susceptance (and thus the permittivity) of blood also is different from the susceptances (and permittivities) of the other types of surrounding or nearby tissues. As a pulse propagates through a particular location, the corresponding increase in the volume of blood results in an increase in the electrical conductivity at the particular location (and more generally an increase in the admittance, or equivalently a decrease in the impedance). Conversely, during the diastolic phase of the cardiac cycle, the corresponding decrease in the volume of blood results in an increase in the electrical resistivity at the particular location (and more generally an increase in the impedance, or equivalently a decrease in the admittance).

A bioimpedance sensor generally functions by applying an electrical excitation signal at an excitation carrier frequency to a region of interest via two or more input electrodes, and detecting an output signal (or output signals) via two or more output electrodes. In some more specific implementations, the electrical excitation signal is an electrical current signal injected into the region of interest via the input electrodes. In some such implementations, the output signal is a voltage signal representative of an electrical voltage response of the tissues in the region of interest to the applied excitation signal. The detected voltage response signal is influenced by the different, and in some instances time-varying, electrical properties of the various tissues through which the injected excitation current signal is passed. In some implementations in which the bioimpedance sensor is operable to monitor blood pressure, heartrate or other cardiovascular characteristics, the detected voltage response signal is amplitude- and phase-modulated by the time-varying impedance (or inversely the admittance) of the underlying arteries, which fluctuates synchronously with the user's heartbeat as described above. To determine various biological characteristics, information in the detected voltage response signal is generally demodulated from the excitation carrier frequency component using various analog or digital signal processing circuits, which can include both passive and active components.

In some examples incorporating ultrasound sensors, measurements of arterial distension may involve directing ultrasonic waves into a limb towards an artery, for example, via one or more ultrasound transducers. Such ultrasound sensors also are configured to receive reflected waves that are based, at least in part, on the directed waves. The reflected waves may include scattered waves, specularly reflected waves, or both scattered waves and specularly reflected waves. The reflected waves provide information about the arterial walls, and thus the arterial distension.

In some implementations, regardless of the type of sensors utilized for the first arterial distension sensor 1006 and the second arterial distension sensor 1008, both the first arterial distension sensor 1006 and the second arterial distension sensor 1008 can be arranged, assembled or otherwise included within a single housing of a single ambulatory monitoring device. As described above, the housing and other components of the monitoring device can be configured such that when the monitoring device is affixed or otherwise physically coupled to a subject, both the first arterial distension sensor 1006 and the second arterial distension sensor 1008 are in contact with or in close proximity to the skin of the user at first and second locations, respectively, separated by a distance $\Delta D$, and in some implementations, along a stretch of the artery between which various arterial properties can be assumed to be relatively constant. In various implementations, the housing of the ambulatory monitoring device is a wearable housing or is incorporated into or integrated with a wearable housing. In some specific implementations, the wearable housing includes (or is connected with) a physical coupling mechanism for removable non-invasive attachment to the user. The housing can be formed using any of a variety of suitable manufacturing processes, including injection molding and vacuum forming, among others. In addition, the housing can be made from any of a variety of suitable materials, including, but not limited to, plastic, metal, glass, rubber and ceramic, or combinations of these or other materials. In particular implementations, the housing and coupling mechanism enable full ambulatory use. In other words, some implementations of the wearable monitoring devices described herein are non-invasive, not physically-inhibiting and generally do not restrict the free uninhibited motion of a subject's arms or legs, enabling continuous or periodic monitoring of cardiovascular characteristics such as blood pressure even as the subject is mobile or otherwise engaged in a physical activity. As such, the ambulatory monitoring device facilitates and enables long-term wearing and monitoring (for example, over days, weeks or a month or more without interruption) of one or more biological characteristics of interest to obtain a better picture of such characteristics over extended durations of time, and generally, a better picture of the user's health.

Figure 11A:
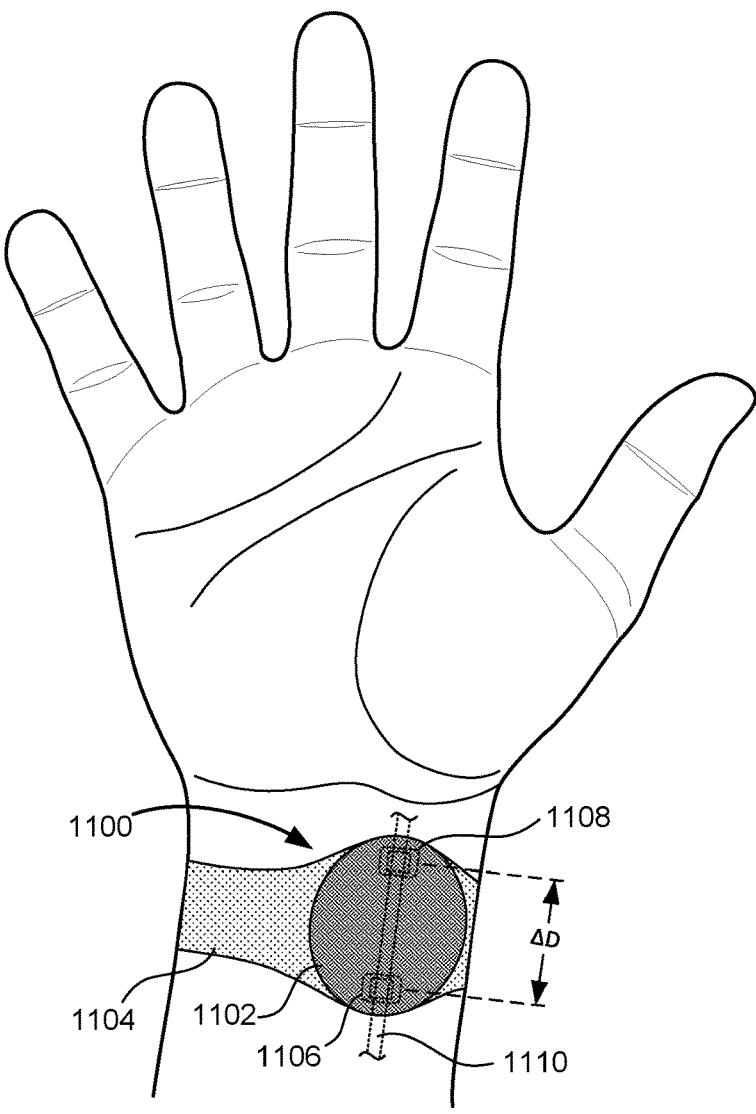
FIG. 11A shows an example ambulatory monitoring device designed to be worn around a wrist according to some implementations.

In some implementations, the ambulatory monitoring device can be positioned around a wrist of a user with a strap or band, similar to a watch or fitness/activity tracker. FIG. 11A shows an example ambulatory monitoring device 1100 designed to be worn around a wrist according to some implementations. In the illustrated example, the monitoring device 1100 includes a housing 1102 integrally formed with, coupled with or otherwise integrated with a wristband 1104. The first and the second arterial distension sensors 1106 and 1108 may, in some instances, each include an instance of the ultrasonic receiver system 302 and a portion of the light source system 304 that are described above with reference to FIG. 3. In this example, the ambulatory monitoring device 1100 is coupled around the wrist such that the first and the second arterial distension sensors 1106 and 1108 within the housing 1102 are each positioned along a segment of the radial artery 1110 (note that the sensors are generally hidden from view from the external or outer surface of the housing facing the subject while the monitoring device is coupled with the subject, but exposed on an inner surface of the housing to enable the sensors to obtain measurements through the subject's skin from the underlying artery). Also as shown, the first and the second arterial distension sensors 1106 and 1108 are separated by a fixed distance ΔD. In some other implementations, the ambulatory monitoring device 1100 can similarly be designed or adapted for positioning around a forearm, an upper arm, an ankle, a lower leg, an upper leg, or a finger (all of which are hereinafter referred to as "limbs") using a strap or band.

Figure 11B:
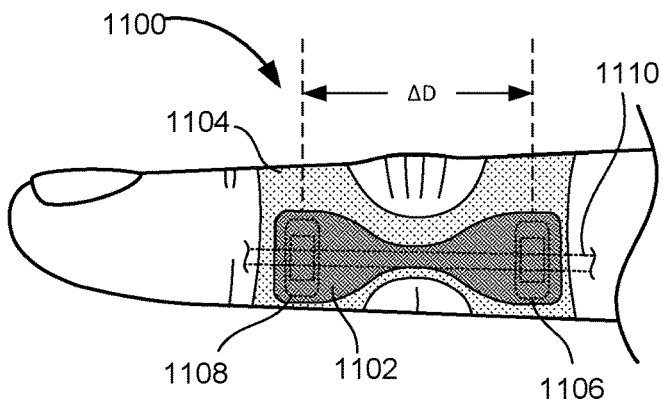
FIG. 11B shows an example ambulatory monitoring device designed to be worn on a finger according to some implementations.

FIG. 11B shows an example ambulatory monitoring device 1100 designed to be worn on a finger according to some implementations. The first and the second arterial distension sensors 1106 and 1108 may, in some instances, each include an instance of the ultrasonic receiver 102 and a portion of the light source system 103 that are described above with reference to FIG. 1.

In some other implementations, the ambulatory monitoring devices disclosed herein can be positioned on a region of interest of the user without the use of a strap or band. For example, the first and the second arterial distension sensors 1106 and 1108 and other components of the monitoring device can be enclosed in a housing that is secured to the skin of a region of interest of the user using an adhesive or other suitable attachment mechanism (an example of a "patch" monitoring device).

Figure 11C:
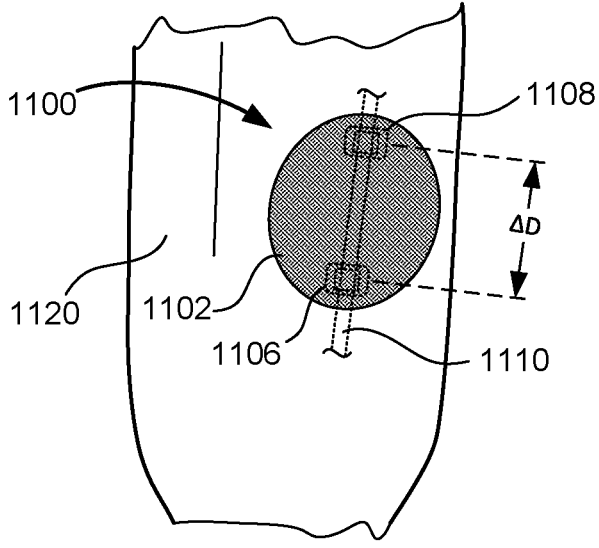
FIG. 11C shows an example ambulatory monitoring device designed to reside on an earbud according to some implementations.

FIG. 11C shows an example ambulatory monitoring device 1100 designed to reside on an earbud according to some implementations. According to this example, the ambulatory monitoring device 1100 is coupled to the housing of an earbud 1120. The first and second arterial distension sensors 1106 and 1108 may, in some instances, each include an instance of the ultrasonic receiver 302 and a portion of the light source system 304 that are described above with reference to FIG. 3.

Implementation examples are described in the following numbered clauses:

1. An apparatus, including: a light source system configured for providing light to a target object on an outer surface of the apparatus; an ultrasonic receiver system configured to receive ultrasonic waves generated by the target object responsive to the light from the light source system; and a control system configured to: receive first sensor signals from at least a first ultrasonic sensor of the ultrasonic receiver system, the first sensor signals including ultrasonic receiver signals; estimate one or more blood vessel features based on the first sensor signals; receive second sensor signals from a second sensor; estimate a pulse wave velocity based, at least in part, on the first sensor signals and the second sensor signals; and estimate blood pressure based, at least in part, on the one or more blood vessel features and the pulse wave velocity.

2. The apparatus of clause 1, where the apparatus is configured to be worn by, or attached to, a person.

3. The apparatus of clause 2, where the apparatus includes a watch, an ear bud, headphones, an ear clip, a chest strap, an arm strap, a head band, or eye wear.

4. The apparatus of clause 2 or clause 3, further including an interface system, where the second sensor signals are received, via the interface system, from a second device.

5. The apparatus of clause 4, where the apparatus is configured to be worn on the person's wrist and where the second device is configured to be worn by, or attached to, the person's finger or the person's arm.

6. The apparatus of clause 4 or clause 5, where the control system is further configured to estimate a distance between the first ultrasonic sensor and the second sensor.

7. The apparatus of any one of clauses 1-6, where the second sensor signals comprise signals from a photoplethysmography sensor, signals from a photoacoustic plethysmography sensor, microphone signals, signals from an accelerometer, capacitive sensor signals, signals from a radio frequency sensor, signals from a magnetic sensor, electrocardiogram signals, signals from an ultrasonic sensor, signals from a pressure sensor, signals from a camera, or combinations thereof.

8. The apparatus of any one of clauses 1-7, where the apparatus includes the second sensor.

9. The apparatus of clause 8, where the apparatus is configured to be worn by, or attached to, a person.

10. The apparatus of clause 8, where the apparatus is a component of a weighing scale, a component of an automobile, a component of an exercise machine or a component of a game controller.

11. The apparatus of any one of clauses 8-10, where the second sensor is a component of the ultrasonic receiver system.

12. The apparatus of clause 11, where the ultrasonic receiver system includes an array of ultrasonic receiver elements.

13. The apparatus of any one of clauses 1-12, where the one or more blood vessel features include blood vessel diameter, blood vessel distension, volumetric flow, or combinations thereof.

14. The apparatus of clause any one of clauses 1-13, where the pulse wave velocity is a regional pulse wave velocity and where the control system is further configured to estimate a local pulse wave velocity.

15. The apparatus of any one of clauses 1-14, where the second sensor signals comprise signals from a sensor array.

16. The apparatus of clause 15, where the sensor array is a two-dimensional sensor array.

17. An apparatus, including: a light source system configured for providing light to a target object on an outer surface of the apparatus; an ultrasonic receiver system configured to receive ultrasonic waves generated by the target object responsive to the light from the light source system; and control means for: receiving first sensor signals from at least a first ultrasonic sensor of the ultrasonic receiver system, the first sensor signals including ultrasonic receiver signals; estimating one or more blood vessel features based on the first sensor signals; receiving second sensor signals from a second sensor; estimating a pulse wave velocity based, at least in part, on the first sensor signals and the second sensor signals; and estimating blood pressure based, at least in part, on the one or more blood vessel features and the pulse wave velocity.

18. The apparatus of clause 17, where the apparatus is configured to be worn by, or attached to, a person.

19. The apparatus of clause 18, where the apparatus includes a watch, an ear bud, headphones, an ear clip, a chest strap, an arm strap, a head band, or eye wear.

20. The apparatus of clause 18 or clause 19, further including an interface system, where the second sensor signals are received, via the interface system, from a second device.

21. A method, including: receiving first sensor signals from at least a first ultrasonic sensor of an ultrasonic receiver system, the first sensor signals including ultrasonic receiver signals corresponding to ultrasonic waves generated by a target object responsive to light from a light source system; estimating one or more blood vessel features based on the first ultrasonic receiver signals; receiving second sensor signals from a second sensor; estimating a pulse wave velocity based, at least in part, on the first ultrasonic receiver signals and the second sensor signals; and estimating blood pressure based, at least in part, on the one or more blood vessel features and the pulse wave velocity.

22. The method of clause 21, where the second sensor signals are received from a second device.

23. The method of clause 22, where the first sensor signals correspond to ultrasonic waves generated within a person's wrist and where the second sensor signals are obtained from the person's finger or the person's arm.

24. The method of clause 22 or clause 23, further including estimating a distance between the first ultrasonic sensor and the second sensor.

25. The method of any one of clauses 21-, where the second sensor signals comprise signals from a photoplethysmography sensor, signals from a photoacoustic plethysmography sensor, microphone signals, signals from an accelerometer, capacitive sensor signals, signals from a radio frequency sensor, signals from a magnetic sensor, electrocardiogram signals, signals from an ultrasonic sensor, signals from a pressure sensor, signals from a camera, or combinations thereof.

26. The method of any one of clauses 21-25, where the one or more blood vessel features include blood vessel diameter, blood vessel distension, volumetric flow, or combinations thereof.

27. The method of any one of clauses 21-26, where the pulse wave velocity is a regional pulse wave velocity and where the method involves estimating a local pulse wave velocity.

28. The method of any one of clauses 21-27, where the second sensor signals comprise signals from a sensor array.

29. The method of clause 28, where the sensor array is a two-dimensional sensor array.

30. The method of any one of clauses 21-29, where receiving the first sensor signals involves receiving signals from an array of ultrasonic sensors of the ultrasonic receiver system.

As used herein, a phrase referring to "at least one of" a list of items refers to any combination of those items, including single members. As an example, "at least one of: a, b, or c" is intended to cover: a, b, c, a-b, a-c, b-c, and a-b-c.

The various illustrative logics, logical blocks, modules, circuits and algorithm processes described in connection with the implementations disclosed herein may be implemented as electronic hardware, computer software, or combinations of both. The interchangeability of hardware and software has been described generally, in terms of functionality, and illustrated in the various illustrative components, blocks, modules, circuits and processes described above. Whether such functionality is implemented in hardware or software depends upon the particular application and design constraints imposed on the overall system.

The hardware and data processing apparatus used to implement the various illustrative logics, logical blocks, modules and circuits described in connection with the aspects disclosed herein may be implemented or performed with a general purpose single- or multi-chip processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, or, any conventional processor, controller, microcontroller, or state machine. A processor also may be implemented as a combination of computing devices, e.g., a combination of a DSP and a microprocessor, a plurality of microprocessors, one or more microprocessors in conjunction with a DSP core, or any other such configuration. In some implementations, particular processes and methods may be performed by circuitry that is specific to a given function.

In one or more aspects, the functions described may be implemented in hardware, digital electronic circuitry, computer software, firmware, including the structures disclosed in this specification and their structural equivalents thereof, or in any combination thereof. Implementations of the subject matter described in this specification also may be implemented as one or more computer programs, i.e., one or more modules of computer program instructions, encoded on a computer storage media for execution by, or to control the operation of, data processing apparatus.

If implemented in software, the functions may be stored on or transmitted over as one or more instructions or code on a computer-readable medium, such as a non-transitory medium. The processes of a method or algorithm disclosed herein may be implemented in a processor-executable software module which may reside on a computer-readable medium. Computer-readable media include both computer storage media and communication media including any medium that may be enabled to transfer a computer program from one place to another. Storage media may be any available media that may be accessed by a computer. By way of example, and not limitation, non-transitory media may include RAM, ROM, EEPROM, CD-ROM or other optical disk storage, magnetic disk storage or other magnetic storage devices, or any other medium that may be used to store desired program code in the form of instructions or data structures and that may be accessed by a computer. Also, any connection may be properly termed a computer-readable medium. Disk and disc, as used herein, includes compact disc (CD), laser disc, optical disc, digital versatile disc (DVD), floppy disk, and Blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and instructions on a machine readable medium and computer-readable medium, which may be incorporated into a computer program product.

Various modifications to the implementations described in this disclosure may be readily apparent to those having ordinary skill in the art, and the generic principles defined herein may be applied to other implementations without departing from the spirit or scope of this disclosure. Thus, the disclosure is not intended to be limited to the implementations shown herein, but is to be accorded the widest scope consistent with the claims, the principles and the novel features disclosed herein. The word "exemplary" is used exclusively herein, if at all, to mean "serving as an example, instance, or illustration." Any implementation described herein as "exemplary" is not necessarily to be construed as preferred or advantageous over other implementations.

Certain features that are described in this specification in the context of separate implementations also may be implemented in combination in a single implementation. Conversely, various features that are described in the context of a single implementation also may be implemented in multiple implementations separately or in any suitable subcombination. Moreover, although features may be described above as acting in certain combinations and even initially claimed as such, one or more features from a claimed combination may in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems may generally be integrated together in a single software product or packaged into multiple software products. Additionally, other implementations are within the scope of the following claims. In some cases, the actions recited in the claims may be performed in a different order and still achieve desirable results.

It will be understood that unless features in any of the particular described implementations are expressly identified as incompatible with one another or the surrounding context implies that they are mutually exclusive and not readily combinable in a complementary and/or supportive sense, the totality of this disclosure contemplates and envisions that specific features of those complementary implementations may be selectively combined to provide one or more comprehensive, but slightly different, technical solutions. It will therefore be further appreciated that the above description has been given by way of example only and that modifications in detail may be made within the scope of this disclosure.

Various modifications to the implementations described in this disclosure may be readily apparent to those skilled in the art, and the generic principles defined herein may be applied to other implementations without departing from the spirit or scope of this disclosure. Thus, the following claims are not intended to be limited to the implementations shown herein, but are to be accorded the widest scope consistent with this disclosure, the principles and the novel features disclosed herein.

Additionally, certain features that are described in this specification in the context of separate implementations also can be implemented in combination in a single implementation. Conversely, various features that are described in the context of a single implementation also can be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Further, the drawings may schematically depict one more example processes in the form of a flow diagram. However, other operations that are not depicted can be incorporated in the example processes that are schematically illustrated. For example, one or more additional operations can be performed before, after, simultaneously, or between any of the illustrated operations. Moreover, various ones of the described and illustrated operations can itself include and collectively refer to a number of sub-operations. For example, each of the operations described above can itself involve the execution of a process or algorithm. Furthermore, various ones of the described and illustrated operations can be combined or performed in parallel in some implementations. Similarly, the separation of various system components in the implementations described above should not be understood as requiring such separation in all implementations. As such, other implementations are within the scope of the following claims. In some cases, the actions recited in the claims can be performed in a different order and still achieve desirable results.

What is claimed is:
1. An apparatus, comprising:
a light source system configured for providing light to a target blood vessel adjacent to an outer surface of the apparatus;
an ultrasonic receiver system configured to receive ultrasonic waves generated by the target blood vessel responsive to the light from the light source system;
a first ultrasonic sensor at a first location corresponding to a position along the target blood vessel;
a second sensor at a second location corresponding to a different position along the target blood vessel; and a control system configured to:

receive first sensor signals from at least the first ultrasonic sensor of the ultrasonic receiver system, the first sensor signals comprising ultrasonic receiver signals;

estimate one or more blood vessel features of the target blood vessel based on the first sensor signals;

receive second sensor signals from the second sensor of the apparatus, the second sensor signals corresponding to the target blood vessel, the second sensor having a fixed second sensor position relative to a first sensor position;

estimate a pulse wave velocity based, at least in part, on the first sensor signals and the second sensor signals; and estimate blood pressure based, at least in part, on the one or more blood vessel features and the pulse wave velocity.

2. The apparatus of claim 1, wherein the apparatus is configured to be worn by, or attached to, a person.

3. The apparatus of claim 2, wherein the apparatus comprises a watch, an ear bud, headphones, an ear clip, a chest strap, an arm strap, a head band, or eye wear.

4. The apparatus of claim 2, further comprising an interface system, wherein the second sensor signals are received, via the interface system, from a second device.

5. The apparatus of claim 4, wherein the apparatus is configured to be worn on the person's wrist and wherein the second device is configured to be worn by, or attached to, the person's finger or the person's arm.

6. The apparatus of claim 4, wherein the control system is further configured to estimate a distance between the first ultrasonic sensor and the second sensor.

7. The apparatus of claim 1, wherein the second sensor signals comprise signals from a photoplethysmography sensor, signals from a photoacoustic plethysmography sensor, microphone signals, signals from an accelerometer, capacitive sensor signals, signals from a radio frequency sensor, signals from a magnetic sensor, electrocardiogram signals, signals from an ultrasonic sensor, signals from a pressure sensor, signals from a camera, or combinations thereof.

8. The apparatus of claim 1, wherein the second sensor position is more than 50 millimeters from the first sensor position.

9. The apparatus of claim 8, wherein the apparatus is configured to be worn by, or attached to, a person.

10. The apparatus of claim 8, wherein the apparatus is a component of a weighing scale, a component of an automobile, a component of an exercise machine or a component of a game controller.

11. The apparatus of claim 8, wherein the second sensor is a component of the ultrasonic receiver system.

12. The apparatus of claim 11, wherein the ultrasonic receiver system includes an array of ultrasonic receiver elements.

13. The apparatus of claim 1, wherein the one or more blood vessel features include blood vessel diameter, blood vessel distension, volumetric flow, or combinations thereof.

14. The apparatus of claim 1, wherein the pulse wave velocity is a regional pulse wave velocity and wherein the control system is further configured to estimate a local pulse wave velocity.

15. The apparatus of claim 1, wherein the second sensor signals comprise signals from a sensor array.

16. The apparatus of claim 15, wherein the sensor array is a two-dimensional sensor array.

17. An apparatus, comprising:

a light source system configured for providing light to a target blood vessel adjacent to an outer surface of the apparatus;

an ultrasonic receiver system configured to receive ultrasonic waves generated by the target blood vessel responsive to the light from the light source system;

a first ultrasonic sensor at a first location corresponding to a position along the target blood vessel;

a second sensor at a second location corresponding to a different position along the target blood vessel; and control means for:

receiving first sensor signals from at least the first ultrasonic sensor of the ultrasonic receiver system, the first sensor signals comprising ultrasonic receiver signals;

estimating one or more blood vessel features based on the first sensor signals;

receiving second sensor signals from the second sensor, the second sensor signals corresponding to the blood vessel;

estimating a pulse wave velocity based, at least in part, on the first sensor signals and the second sensor signals; and estimating blood pressure based, at least in part, on the one or more blood vessel features and the pulse wave velocity, wherein the apparatus comprises an ear bud, headphones or an ear clip configured to be worn by, or attached to, a person.

18. The apparatus of claim 17, further comprising an interface system, wherein the second sensor signals are received, via the interface system, from a second device.

19. A method, comprising:

receiving first sensor signals from at least a first ultrasonic sensor of an ultrasonic receiver system, the first sensor signals comprising ultrasonic receiver signals corresponding to ultrasonic waves generated by a blood vessel responsive to light from a light source system, the first ultrasonic sensor positioned at a first location corresponding to a position along the blood vessel;

estimating one or more blood vessel features based on the first ultrasonic receiver signals;

receiving second sensor signals from a second sensor, the second sensor signals corresponding to the blood vessel, the second sensor positioned at a second location corresponding to a different position along the blood vessel;

estimating a pulse wave velocity based, at least in part, on the first ultrasonic receiver signals and the second sensor signals; and estimating blood pressure based, at least in part, on the one or more blood vessel features and the pulse wave velocity.

20. The method of claim 19, wherein the second sensor signals are received from a second device.

21. The method of claim 20, wherein the first sensor signals correspond to ultrasonic waves generated within a person's wrist and wherein the second sensor signals are obtained from the person's finger or the person's arm.

22. The method of claim 20, further comprising estimating a distance between the first ultrasonic sensor and the second sensor.

23. The method of claim 19, wherein the second sensor signals comprise signals from a photoplethysmography sensor, signals from a photoacoustic plethysmography sensor, microphone signals, signals from an accelerometer, capacitive sensor signals, signals from a radio frequency sensor, signals from a magnetic sensor, electrocardiogram signals, signals from an ultrasonic sensor, signals from a pressure sensor, signals from a camera, or combinations thereof.

24. The method of claim 19, wherein the one or more blood vessel features include blood vessel diameter, blood vessel distension, volumetric flow, or combinations thereof.

25. The method of claim 19, wherein the pulse wave velocity is a regional pulse wave velocity and wherein the method involves estimating a local pulse wave velocity.

26. The method of claim 19, wherein the second sensor signals comprise signals from a sensor array.

27. The method of claim 26, wherein the sensor array is a two-dimensional sensor array.

28. The method of claim 19, wherein receiving the first sensor signals involves receiving signals from an array of ultrasonic sensors of the ultrasonic receiver system.

\* \* \* \* \*